US012616613B2

(12) United States Patent
Van de Pas et al.

(10) Patent No.: US 12,616,613 B2
(45) Date of Patent: May 5, 2026

(54) APPARATUS FOR FORMING AND APPLYING A PLEATED CORE WRAP

(71) Applicant: Curt G. Joa, Inc., Sheboygan Falls, WI (US)

(72) Inventors: Hubert P. Van de Pas, Kiel, WI (US); Randy J. Teresinski, Jr., Sheboygan Falls, WI (US); Christopher S. Lawrence, Elkhart Lake, WI (US); Jeffrey W. Fritz, Plymouth, WI (US); Cory D. Veldman, Plymouth, WI (US); Zachary J. Giffey, Plymouth, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 77 days.

(21) Appl. No.: 18/837,829

(22) PCT Filed: Feb. 23, 2023

(86) PCT No.: PCT/US2023/063175

§ 371 (c)(1),
(2) Date: Aug. 12, 2024

(87) PCT Pub. No.: WO2023/164586

PCT Pub. Date: Aug. 31, 2023

(65) Prior Publication Data

US 2025/0143932 A1     May 8, 2025

Related U.S. Application Data

(60) Provisional application No. 63/268,618, filed on Feb. 28, 2022.

(51) Int. Cl.
*A61F 13/15*     (2006.01)

(52) U.S. Cl.
CPC .. *A61F 13/15658* (2013.01); *A61F 13/15682* (2013.01); *A61F 2013/1591* (2013.01)

(58) Field of Classification Search
CPC ............ A61F 13/15658; A61F 13/1565; A61F 13/5315
See application file for complete search history.

(56) References Cited

U.S. PATENT DOCUMENTS 5,076,774 A * 12/1991 Farrington ........ A61F 13/15634
19/301
6,451,001 B2 9/2002 Kumasaka
(Continued)

FOREIGN PATENT DOCUMENTS

EP     3711731 A1     2/2021
JP     2018057786 A     4/2018
(Continued)

OTHER PUBLICATIONS

International Search Report and Written Opinion for corresponding PCT Application No. PCT/US2023/063175, mailed Jul. 6, 2023.

*Primary Examiner* — Barbara J Musser
(74) *Attorney, Agent, or Firm* — Quarles & Brady, LLP

(57)     ABSTRACT

An apparatus for forming and applying a pleated core wrap includes a feeding mechanism configured to feed a continuous web of material in a machine direction and a pleating unit configured to form one or more continuous folds in the continuous web of material, so as to form a continuous pleated web of material with a portion of the web of material overlapped in a cross-machine direction. A core-forming drum receives the continuous pleated web of material, the core-forming drum including at least one depression provided on an outer circumferential surface thereof, the depression having a floor having one or more inserts protruding radially outward therefrom. A vacuum system provided a vacuum to the depression that is communicated (Continued)

through the floor to suction the continuous pleated web of material down into the depression, with regions of the continuous pleated web of material separating upon being suctioned down into the depression.

20 Claims, 14 Drawing Sheets

(56)　　　　　　References Cited

U.S. PATENT DOCUMENTS

| | | | |
|---|---|---|---|
| 8,979,815 | B2 | 3/2015 | Roe et al. |
| 9,216,118 | B2 | 12/2015 | Roe et al. |
| 9,532,906 | B2 | 1/2017 | Bauduin et al. |
| 9,707,135 | B2 | 7/2017 | Sheldon et al. |
| 10,137,039 | B2 | 11/2018 | Stelzig et al. |
| 2002/0182396 | A1 | 12/2002 | DeLucia et al. |
| 2005/0147711 | A1 | 7/2005 | Walter et al. |
| 2006/0065354 | A1 | 3/2006 | Mischler et al. |
| 2016/0175169 | A1 | 6/2016 | Bianchi et al. |
| 2017/0079857 | A1 | 3/2017 | Willhaus et al. |
| 2019/0053956 | A1 | 2/2019 | Nakamura et al. |
| 2020/0078229 | A1 | 3/2020 | Van Ingelgem et al. |
| 2025/0161121 | A1* | 5/2025 | Nelson ................ A61F 13/1565 |
| 2025/0162302 | A1* | 5/2025 | Bäck ................... A61F 13/5323 |

FOREIGN PATENT DOCUMENTS

| | | | |
|---|---|---|---|
| WO | 2010071508 | A1 | 6/2010 |
| WO | 2011077323 | A1 | 6/2011 |

* cited by examiner

VACUUM ZONE

VACUUM ZONE

VACUUM ZONE

APPARATUS FOR FORMING AND APPLYING A PLEATED CORE WRAP

CROSS REFERENCE TO RELATED APPLICATION

This application is the U.S. National Stage of PCT/US2023/063175 with international filing date of Feb. 23, 2023, and which claims priority to U.S. Provisional Application No. 63/268,618 filed on Feb. 28, 2022, the contents of which are incorporated by reference in their entireties.

BACKGROUND OF THE INVENTION

Embodiments of the invention relate to an apparatus for forming and applying a pleated core web in the manufacture of disposable absorbent articles such as diapers or incontinence control garments. More particularly, embodiments of the invention relate to such an apparatus forming a pleated core wrap and applying the pleated core wrap into one or more depressions of a core forming drum in the manufacture of absorbent cores, with the depression(s) including one or more inserts therein that provide for the formation of one or more channels in the absorbent cores. As the pleated core wrap is drawn down into a depression of the core forming drum, the pleats in the core wrap unfold so as to allow for the core wrap to better conform to the depression, including conforming about the insert(s) therein.

Disposable absorbent articles, such as diapers, incontinence type articles, or feminine hygiene products, are typically formed from a combination of multiple web layers, absorbent structures, and elastic elements. The articles may thus include a thin flexible liquid impermeable backing sheet on which a permeable nonwoven sheet is overlayed. An absorbent core is disposed between the two sheets and the sheets are adhered at their edges to form a unitary article that prevents liquid body exudates from seeping out of the edges of the article.

In disposable absorbent articles as referenced above, the absorbent core is typically formed of an absorbent material (e.g., granules of superabsorbent polymer material (SAP)) contained inside a mixture of containment cellulose pulp (fluff) and absorbent material binder. The absorbent material is sandwiched between or wrapped by one or more layers of nonwoven fabric. To improve performance in terms of absorption, comfort and distribution of absorbed liquids, the absorbent core may be provided with longitudinal channels formed therein that are free or substantially free of absorbent material between the two layers of nonwoven fabric.

In the manufacture of channeled absorbent cores, a continuous web of nonwoven material, or base web, is fed onto a rotating core forming drum that includes a continuous three-dimensional fluff receiving pocket or depression (or a plurality of discrete, three-dimensional fluff receiving pockets or depressions) on an outer circumferential surface thereof. The base web is laid down onto the core forming drum and drawn down into the depression(s) via a vacuum system internal to the core forming drum, with the vacuum creating a suction that attracts the base web down into the depression(s). In the depression(s), the base web conforms to inserts (i.e., protrusions) positioned therein that extend radially outward from a floor of the depressions. Absorbent material, such as SAP, fluff, or a mixture thereof, is then blown into the depression(s) and on top of the base web. The absorbent material is caused to adhere to the base web by way of an adhesive previously applied onto the base web, in combination with the suction provided by the vacuum system. A cover web is then applied over the base web and over the pocket(s) of absorbent material provided thereon. The cover web is then bonded to the base web via adhesive or an adhesive-free bonding means such as mechanical, thermal, or ultrasonic bonding, and bonded to the absorbent material to produce an absorbent core.

Core forming drums designed for the manufacture of higher capacity cores typically include pockets designed with deeper depression(s) and inserts having an increased height corresponding to the increased depression depth. When exposed to these pocket geometries, the base web may experience higher stress and tension when caused to conform to the depression(s) and about the inserts. That is, as the base web is initially laid down into a depression in a flat configuration, and then caused to conform under vacuum to the increased depression depth and insert height, the base web experiences stress and tension in the cross-machine direction. This increased stress and tension placed on the base web can cause the web to tear at locations corresponding to the depression inserts.

It is therefore desirable to provide an improved apparatus for forming and applying a nonwoven base web to a core forming drum that reduces the stress and tension placed on the base web as the web is laid down into pocket geometries including depressions and one or more channel-forming inserts on the core forming drum.

BRIEF DESCRIPTION OF THE INVENTION

Embodiments of the invention are expressed and characterized in the independent claims, while the dependent claims explain other characteristics and variants of the invention. The characteristics and variants described in the dependent claims may be used in combination with or in isolation from each other, according to embodiments of the invention.

In accordance with some embodiments, an apparatus includes a feeding mechanism configured to feed a continuous web of material in a machine direction and a pleating unit configured to form one or more folds in the continuous web of material, each of the one or more folds comprising a continuous fold running in the machine direction so as to form a continuous pleated web of material with a portion of the web of material overlapped in a cross-machine direction. The apparatus also includes a core-forming drum rotating in the machine direction and positioned downstream in the machine direction from the pleating unit to receive the continuous pleated web of material, the core-forming drum comprising at least one depression provided on an outer circumferential surface of the core forming drum, with the at least one depression including a floor having one or more inserts protruding radially outward therefrom. The apparatus further includes a vacuum system configured to provide a vacuum to the at least one depression, the vacuum communicated through the floor to suction the continuous pleated web of material down into the at least one depression, with regions of the continuous pleated web of material separating upon being suctioned down into the at least one depression.

In some embodiments, an adhesive applicator is positioned downstream in the machine direction from the pleating unit, the adhesive applicator configured to apply adhesive to non-overlapped portions of a top surface of the pleated web of material.

In some embodiments, the adhesive applicator is configured to apply adhesive to non-overlapped portions of the top surface of the pleated web of material that are offset from the one or more inserts in the cross-machine direction.

3

In some embodiments, a heated roller is positioned between the pleating unit and the adhesive applicator, the heated roller configured to apply heat to the continuous pleated web of material to set the one or more folds thereof.

In some embodiments, a bonding unit positioned between the pleating unit and the adhesive applicator, the bonding unit configured to tack bond the continuous pleated web of material to set the one or more folds thereof.

In some embodiments, the pleating unit of the apparatus includes a top roll and a bottom roll positioned to form a nip therebetween through which the continuous web of material is fed, the top and bottom rolls including features thereon that act on the continuous web of material to predispose the continuous web of material to folding. The pleating unit also includes a folding board and one or more folding skis positioned downstream in the machine direction from the top and bottom rolls, the folding board and the one or more folding skis positioned in an overlapped arrangement. The continuous web of material is controlled and constrained into a pleated shape when traveling in the machine direction as it passes the one or more folding skis and the folding board.

In some embodiments, the one or more inserts comprise a first insert and a second insert each generally aligned in the machine direction, with the first insert and the second insert spaced apart in the cross-machine direction by a first distance.

In some embodiments, the pleating unit is configured to form a first fold in the continuous web of material running in the machine direction and form a second fold in the continuous web of material running in the machine direction, wherein the first fold and the second fold are spaced apart in the cross-machine direction by a second distance greater than the first distance.

In some embodiments, the pleating unit is configured to form a first pair of folds in the continuous web of material in a first pleated area, each fold of the first pair of folds running in the machine direction, and form a second pair of folds in the continuous web of material in a second pleated area, each fold of the second pair of folds running in the machine direction. The folds of the first pair of folds are located so as to be positioned on opposing sides of the first insert when the continuous pleated web of material is fed into the at least one depression, and the folds of the second pair of folds are located so as to be positioned on opposing sides of the second insert when the continuous pleated web of material is fed into the at least one depression.

In some embodiments, the at least one depression comprises a center region positioned between the pair of inserts in the cross-machine direction and side regions positioned on opposing side of the center region and outside of the pair of inserts in the cross-machine direction, and the vacuum system is configured to selectively communicate a vacuum to the center region and the side regions.

In some embodiments, the vacuum system comprises a first vacuum shoe positioned at a lay-down zone location of the core-forming drum where the continuous pleated web of material is fed onto the core-forming drum, the first vacuum shoe configured to communicate a vacuum to the center region and block a vacuum to the side regions. The vacuum system also comprises a second vacuum shoe positioned downstream in the machine direction from the first vacuum shoe, the second vacuum shoe configured to communicate a vacuum to the side regions and block a vacuum to the center region.

In some embodiments, each of the first insert and the second insert has an inverted triangular shape.

In some embodiments, each of the first insert and the second insert has one or more spaces or ventilation channels formed therein that provides for airflow therethrough.

In accordance with other embodiments, an apparatus includes a feeding mechanism configured to feed a continuous web of material in a machine direction and a core-forming drum rotating in the machine direction and positioned downstream in the machine direction from the feeding mechanism to receive the continuous web of material, the core-forming drum comprising at least one depression provided on an outer circumferential surface of the core-forming drum, with the at least one depression including a floor having one or more inserts protruding radially outward therefrom. The apparatus also includes a vacuum system that provides a vacuum to the at least one depression, the vacuum communicated through the floor to suction the continuous web of material down into the at least one depression, and wherein the vacuum system is configured to selectively control communication of the vacuum to a plurality of cross-machine direction arranged regions of the at least one depression to provide a multi-stage, progressive laydown of the continuous web of material into the at least one depression.

In some embodiments, the one or more inserts comprise a first insert and a second insert each aligned in the machine direction, with the first insert and the second insert spaced apart in the cross-machine direction by a first distance. In selectively controlling communication of the vacuum to a plurality of cross-machine direction arranged regions of the at least one depression, the vacuum system is configured to initially communicate a vacuum to a center region positioned between the pair of inserts and subsequently communicate a vacuum to side regions positioned on opposing side of the center region and outside of the pair of inserts in the cross-machine direction, or to both the side regions and the center region.

In some embodiments, the vacuum system comprises one or more vacuum shoes configured to communicate or block a vacuum to the center region and the side regions.

In some embodiments, a pleating unit is positioned upstream in the machine direction from the core-forming drum, the pleating unit configured to form one or more folds in the continuous web of material, each of the one or more folds comprising a continuous fold running in the machine direction so as to form a continuous pleated web of material with a portion of the web of material overlapped in a cross-machine direction. Regions of the continuous pleated web of material separate during the multi-stage, progressive laydown of the continuous web of material into the at least one depression.

In some embodiments, an adhesive applicator is positioned downstream in the machine direction from the pleating unit, the adhesive applicator configured to apply adhesive to non-overlapped portions of a top surface of the pleated web of material.

In some embodiments, the adhesive applicator is configured to apply adhesive to non-overlapped portions of the top surface of the pleated web of material that are offset from the one or more inserts in the cross-machine direction.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the invention are directed to an apparatus for forming and applying a pleated core wrap during the manufacture of an absorbent pad. The formation of the pleated core wrap, and subsequent application thereof onto a forming drum, allows the pleated core wrap to better conform to one or more depressions in the forming drum and the inserts included in the depression(s). The improved apparatus disclosed herein reduces the stress and tension placed on the core wrap as the web is laid down into the depression(s), thereby reducing the occurrence of tears in the core wrap during manufacturing of the absorbent pads.

Although the disclosure hereof is provided in sufficient detail to enable those skilled in the art to practice the invention, the physical embodiments herein disclosed merely exemplify the invention, which may be embodied in other specific structures. While the preferred embodiments have been described, the details may be changed without departing from the invention.

Figure 1A:
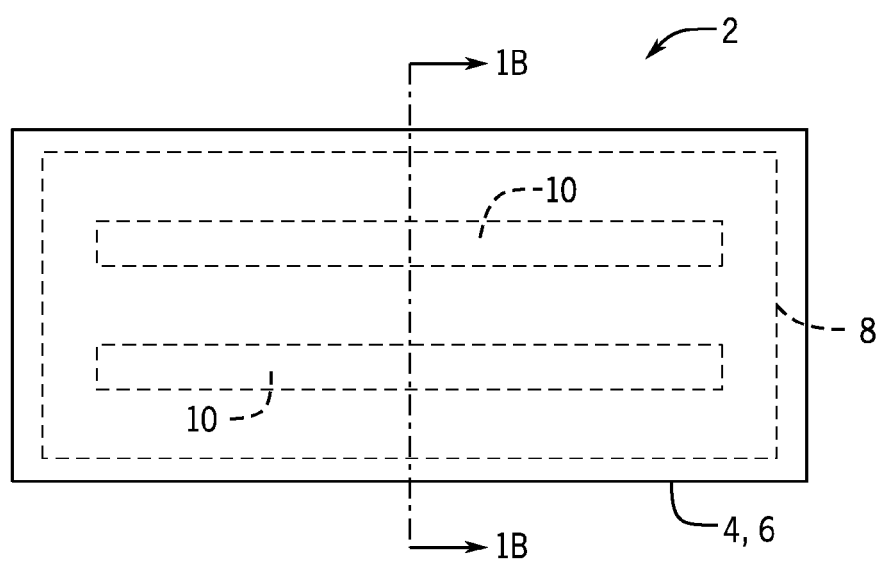
FIG. 1A depicts a top view of a channeled absorbent core that that may be formed via an apparatus of the invention.
Figure 1B:
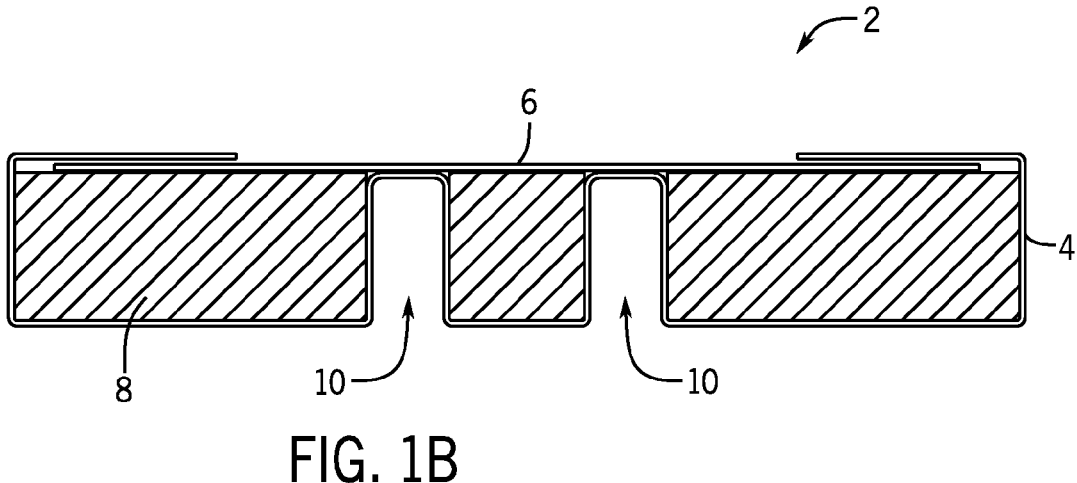
FIG. 1B depicts a cross-sectional view of the channeled absorbent core of FIG. 1A, taken along line 1B.

Referring now to FIGS. 1A and 1B, an example absorbent core 2 is illustrated that may be produced (in part) via use of an apparatus for forming and applying a pleated core wrap, as described hereafter. The absorbent core 2 illustrated in FIG. 1 may be incorporated into disposable absorbent articles such as baby diapers or adult incontinence products, for example.

The absorbent core 2 includes a first layer 4, a second layer 6, and an absorbent material 8 interposed between the first and second layers 4, 6. The first and second layers 4, 6 are made, for example, of a nonwoven material and are joined to each other. The absorbent material 8 is composed of one or more absorbent materials, such as cellulose fibers (fluff) and/or superabsorbent material (SAP) for example, and is fixed between the first and the second layer 4, 6.

In the example illustrated, the absorbent core 2 has two zones or channels 10 which are free or substantially free of absorbent material. In some embodiments, the first and second layers 4, 6 are joined directly to each other, such as via adhesive or an adhesive-free bond. In these embodiments, the first layer 4 and the second layer 6 are directly attached to each other at the zones or channels 10. In alternative embodiments, the first and second layers 4, 6 may remain unattached to one another and, in some cases, remain physically spaced apart from one another at the channels 10.

Figure 2:
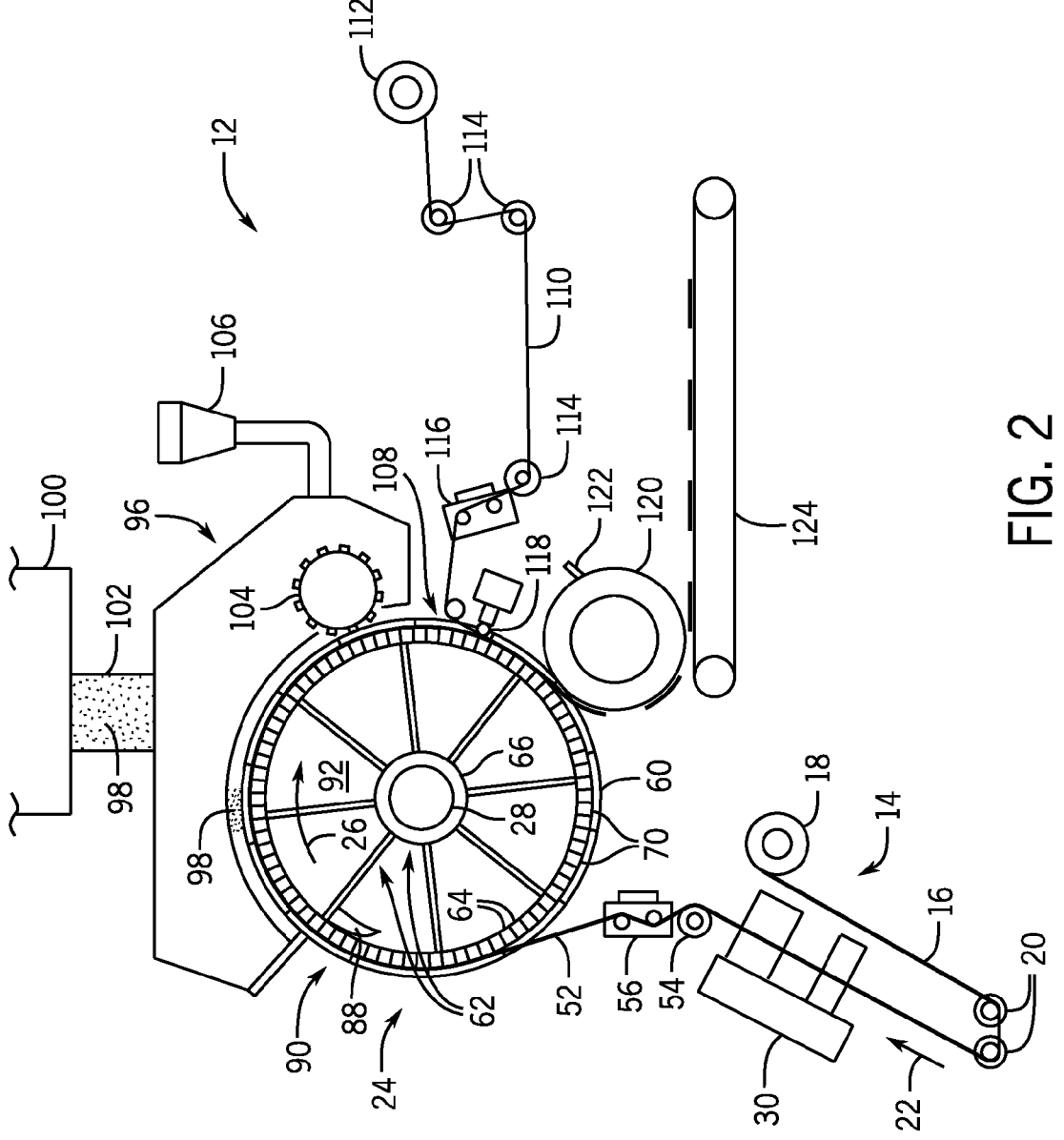
FIG. 2 is a schematic view illustrating the layout of an apparatus for forming a pleated core wrap and applying the pleated core wrap onto a forming drum, according to an embodiment of the invention.

Referring now to FIG. 2, a schematic diagram of an example apparatus 12 is illustrated that, in one implementation, may form absorbent cores 2 as shown in FIG. 1. In the embodiment of FIG. 2, a feed mechanism 14 is provided that supplies and advances a continuous web of nonwoven material 16, which is hereafter referred to as a "form-on web 16" for purposes of simplicity. The feed mechanism 14 may thus include a material roll 18 from which the form-on web 16 may be unwound, along with one or more material handling rollers 20 that advance the form-on web 16 in a machine direction 22. As will be explained in further detail below, the form-on web 16 is fed toward a core forming drum 24 (hereafter "forming drum 24") and drawn onto depressions in the forming drum 24 by vacuum pressure. The forming drum 24 rotates in the direction of arrow 26 (i.e., in the machine direction 22) about a driveshaft 28, advancing the form-on web 16 through one or more absorbent core forming stages, ultimately resulting in the absorbent cores 2 that are dispensed off of the forming drum 24. According to embodiments, the absorbent cores 2 may be formed on the forming drum 24 as a continuous ribbon or continuous pad or as discrete pads.

In some embodiments, the form-on web 16 provided by the feed mechanism 14 is a nonwoven material such as a meltblown or spunbond-meltblown-spunbond (SMS) material, although it is recognized that the form-on web 16 may be any suitable woven, nonwoven, or tissue material. The form-on web 16 is at least semi-permeable to airflow, such that air is able to move through the form-on web 16 when fed onto the forming drum 24 so that the form-on web 16 may be secured thereto via vacuum.

As the form-on web 16 is advanced in the machine direction 22, the web 16 is fed into a pleating unit 30 that functions to form one or more folds therein. The pleating unit 30 forms fold(s) in the continuous form-on web 16 that are oriented and run in the machine direction 22. The running fold(s) formed in the machine direction 22 cause one or more portions of the form-on web 16 to overlap in a cross-machine direction 32 (FIGS. 3A-3C), thereby forming a continuous pleated web of material that is subsequently advanced downstream to the forming drum 24.

Figure 3A:
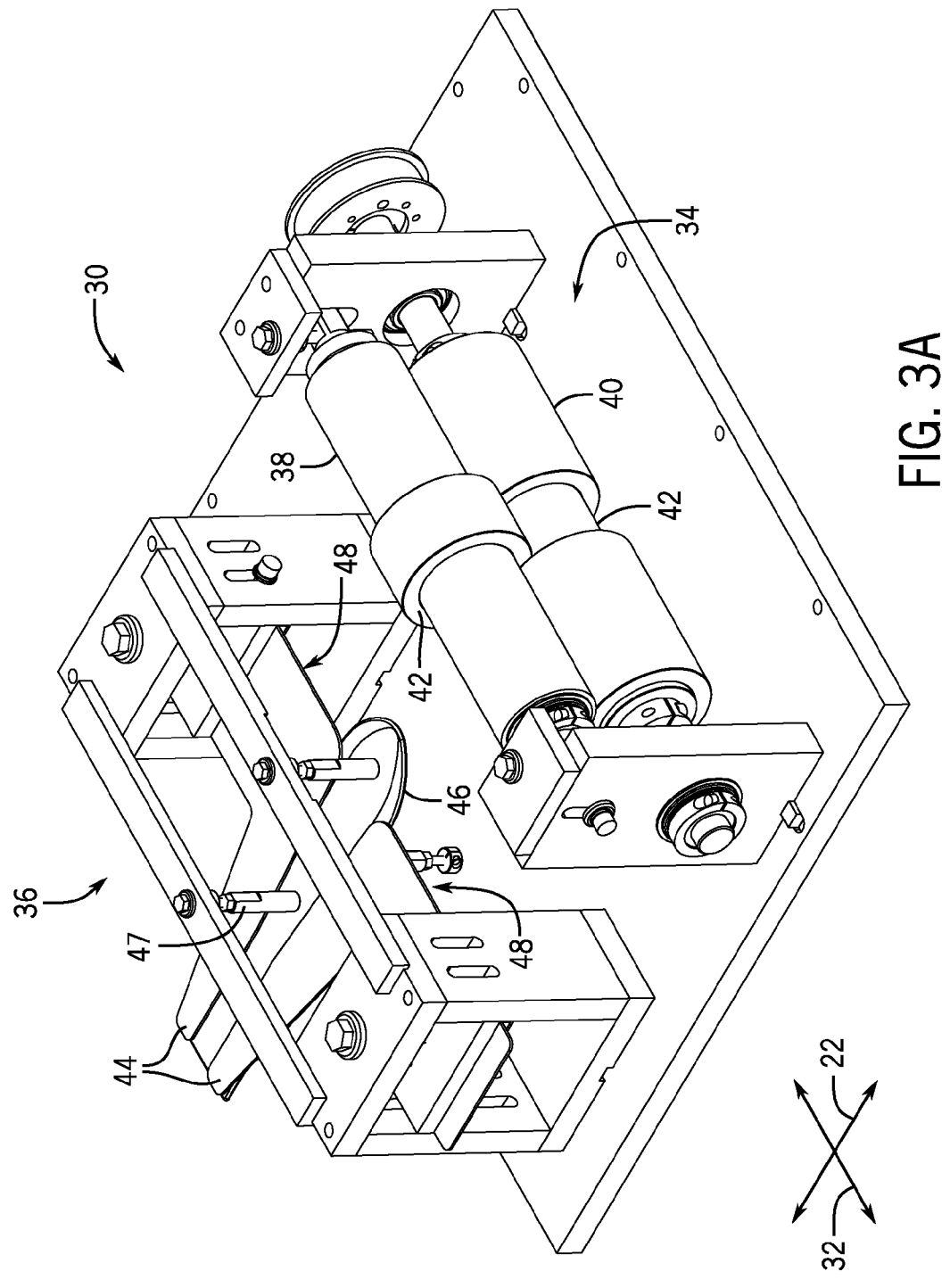
FIG. 3A is a perspective view of a pleating unit included in the apparatus of FIG. 2, according to an embodiment of the invention.
Figure 3B:
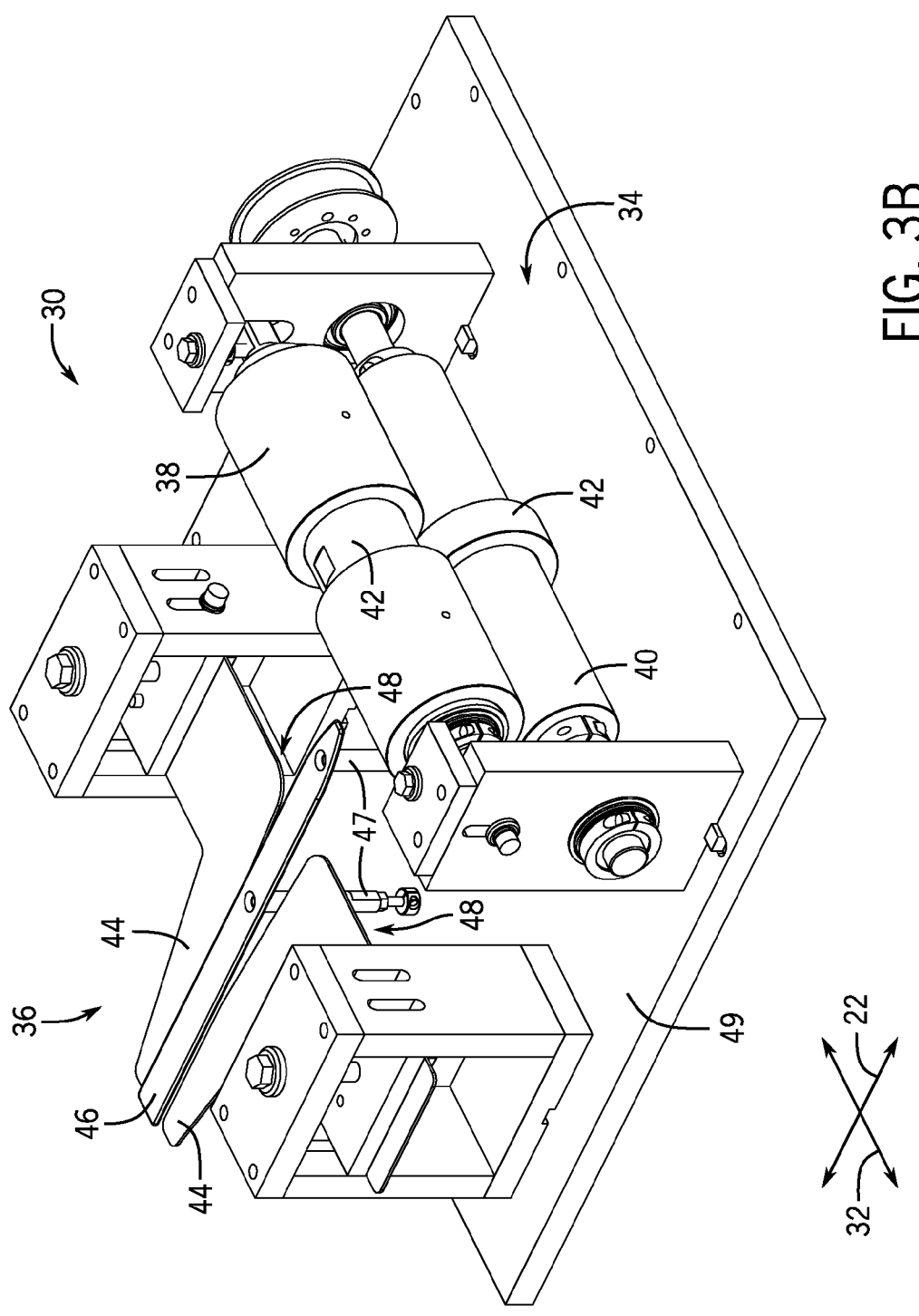
FIG. 3B is a perspective view of a pleating unit included in the apparatus of FIG. 2, according to an embodiment of the invention.
Figure 3C:
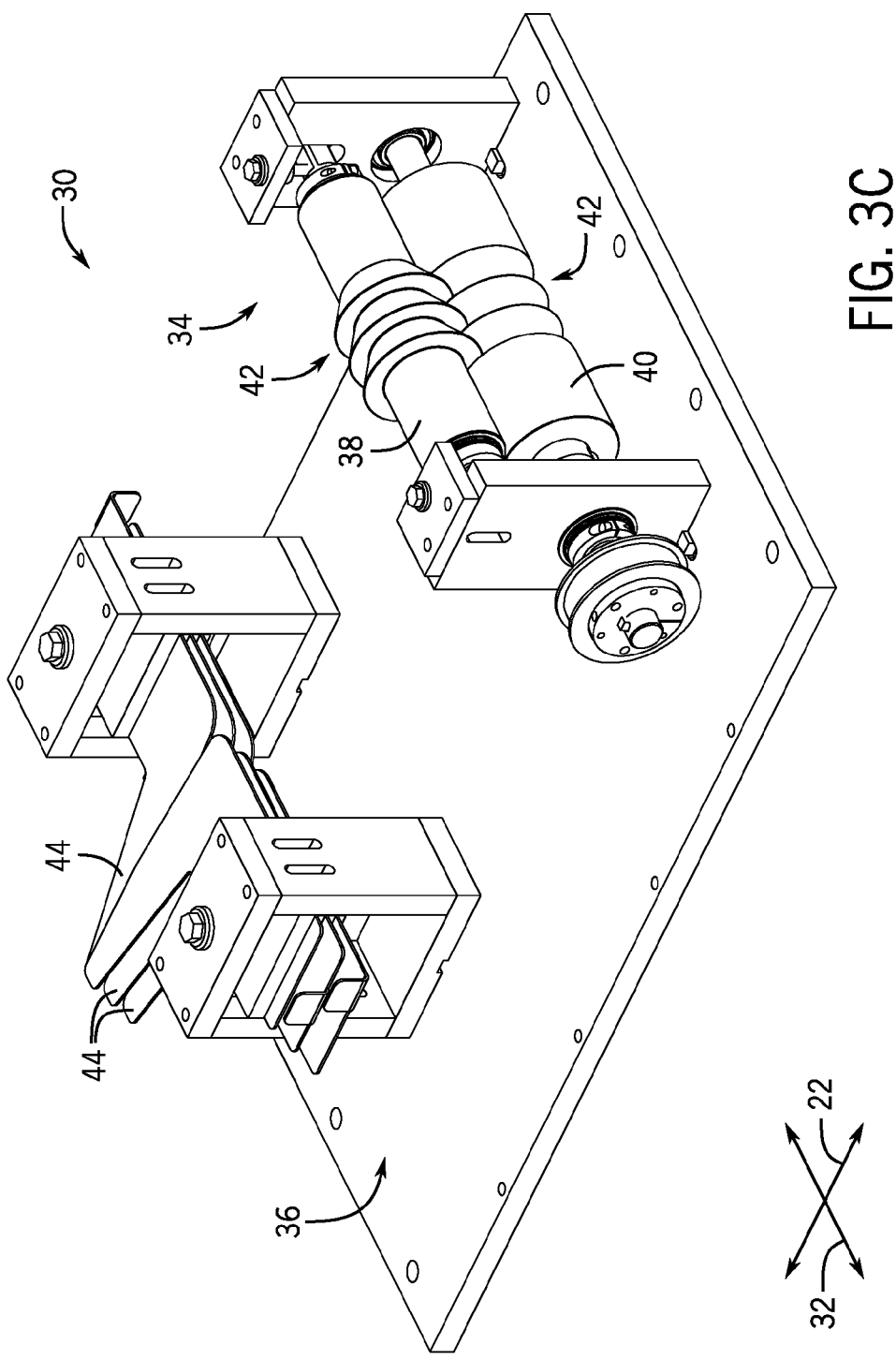
FIG. 3C is a perspective view of a pleating unit included in the apparatus of FIG. 2, according to an embodiment of the invention.

Referring to FIGS. 3A-3C, exemplary pleating units are shown in greater detail such as may be provided for the pleating unit 30. Referring first to FIG. 3A, the pleating unit 30 includes a web entry side 34 and a web exit side 36, with the form-on web 16 being fed into the pleating unit 30 at the web entry side 34 and advancing in the machine direction 22 to the web exit side 36. At the web entry side 34, a top roll 38 and a bottom roll 40 are positioned to form a nip therebetween through which the form-on web 16 is fed. The rolls 38, 40 are configured to include one or more features 42 thereon that circumscribe the face of the rolls 38, 40. The features 42 may be provided as corresponding protrusions and depressions formed in/on the rolls 38, 40 and that make contact with the form-on web 16 as it passes through the nip between the rolls 38, 40. The features 42 function to stress or "break" the form-on web 16 at desired locations (i.e., along break lines) in the cross-machine direction 32 in a manner that better provides for the web to be subsequently folded. As a result, the form-on web 16 is predisposed to be subsequently folded to form pleats.

The form-on web 16 then advances in the machine direction 22 to an arrangement of folding skis 44 and a folding board 46 (held in place by one or more support rods 47) that function to form folds in the form-on web 16 as it runs in the machine direction 22. As shown in FIG. 3A, the folding skis 44 and folding board 46 are positioned in an overlapped arrangement. Each of the folding skis 44 has a generally flat end surface 48 on an upstream facing end thereof that is aligned in the cross-machine direction 32, with a protrusion extending outward therefrom downstream in the machine direction 22. The folding skis 44 are positioned above the folding board 46 and overlap therewith, and the form-on web 16 is aligned with the folding skis 44 in the cross-machine direction 32 so that the breaks formed in the form-on web 16 (by features 42) align with the folding skis 44. As the form-on web 16 travels in the machine direction 22, a central region of the web 16 is fed beneath the folding board 46, while side regions of the web 16 are fed into an area between the folding board 46 and the folding skis 44. The form-on web 16 is then controlled and constrained into a pleated shape when traveling in the machine direction 22 as portions thereof pass below the folding board 46, between the folding skis 44 and the folding board 46, and are guided about and over the folding skis 44. In one embodiment, the folding board 46 preferably remains level over its entire span (in the machine direction 22) while the folding skis 44 are in a plane that declines in the Z-direction as the folding skis 44 extend downstream in the machine direction 22. At the entrance of the folding skis 44, the vertical clearance between the folding skis 44 and the folding board 46 is approximately equal to the thickness of the form-on web 16 and provides sufficient clearance so that portions of the web 16 can be threaded between the folding skis 44 and the folding board 46. At the exit of the folding skis 44, the folding skis 44 interfere with the folding plate 46 in the Z-direction to constrain the pleats of web 20 therebetween.

Referring to FIG. 3B, pleating unit 30 is shown according to another embodiment. The pleating unit 30 is structurally similar to the pleating unit of FIG. 3A, except that the features thereof are arranged in an inverse configuration. That is, at the web entry side 34, the positioning of the top roll 38 and bottom roll 40 (i.e., of the protrusions and depressions formed in/on the rolls 38, 40) is flipped vertically, such that the breaks formed on the form-on web 16 predispose the web to folding in an inverse direction from those that would be formed with the pleating unit of FIG. 3A. The positioning of folding skis 44 and a folding board 46 is also flipped vertically in the pleating unit 30 of FIG. 3B, with the folding board 46 positioned above the folding skis 44 and overlapping therewith, and with the support rod(s) 47 extending up from a base 49 of the pleating unit 30 to support the folding board 46. The form-on web 16 is then controlled and constrained into a pleated shape when traveling in the machine direction 22 as portions thereof pass above the folding board 46, between the folding skis 44 and the folding board 46, and are guided about and beneath the folding skis 44.

Referring R to FIG. 3C, pleating unit 30 is shown according to yet another embodiment. The pleating unit 30 of FIG. 3C differs from the pleating units 30 of FIGS. 3A and 3B in that it forms a greater number of break lines and folds in the form-on web 16. At the web entry side 34, each of the top roll 38 and bottom roll 40 include a plurality of features 42 thereon that interact with each other to cause break lines to be formed on the form-on web 16. The form-on web 16 advances in the machine direction 22 to an arrangement of folding skis 44 that are staggered in the cross-machine direction 32 and further positioned in an overlapped arrangement. Each of the folding skis 44 has a generally flat end surface 48 on an upstream facing end thereof that is aligned in the cross-machine direction 32, with a protrusion extending outward therefrom downstream in the machine direction 22. The form-on web 16 is aligned with the folding skis 44 in the cross-machine direction 32 so that the break lines on the form-on web 16 align with the folding skis 44. The form-on web 16 is controlled and constrained into a pleated shape when traveling in the machine direction 22 as it passes between and over the folding skis 44. In the configuration shown in FIG. 3C, pleating unit 30 is configured to form three (3) folds. It is contemplated that the configuration of pleating unit 30 may be modified to form more or less folds in alternate embodiments.

Figure 4:
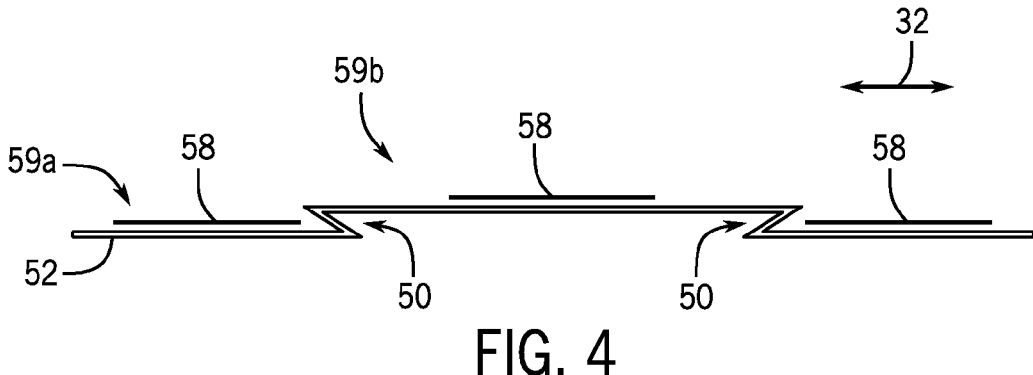
FIG. 4 is a cross-sectional view of a pleated web of nonwoven material that may be provided by any of the pleating units of FIGS. 3A-3C, according to an embodiment of the invention.
Figure 5:
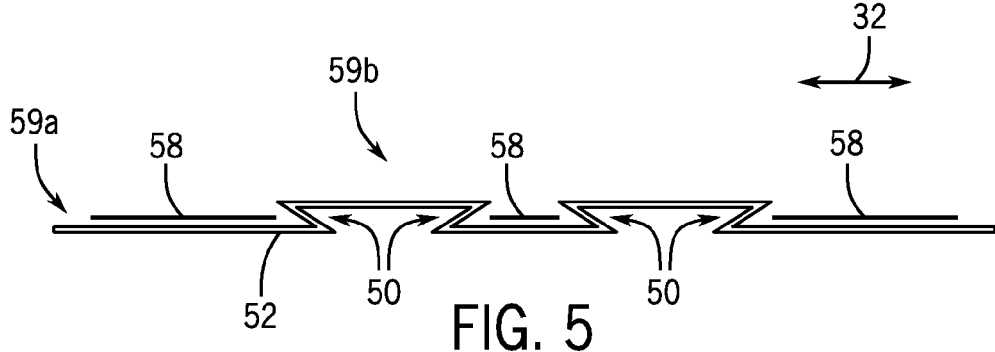
FIG. 5 is a cross-sectional view of a pleated web of nonwoven material that may be provided by any of the pleating units of FIGS. 3A-3C, according to another embodiment of the invention.
Figure 6:
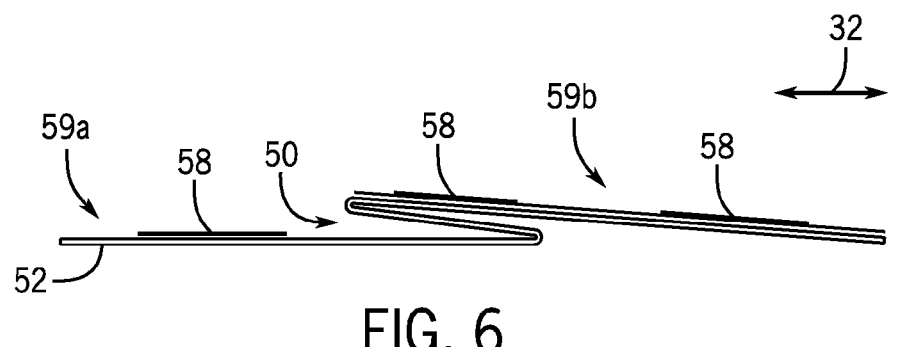
FIG. 6 is a cross-sectional view of a pleated web of nonwoven material that may be provided by any of the pleating units of FIGS. 3A-3C, according to another embodiment of the invention.

According to an embodiment, the number and/or location of folding skis 44 and folding boards 46 in the pleating units 30 of FIGS. 3A-3C are adjustable to control the number and/or location of the folds formed in the form-on web 16. That is, the number and location (in the cross-machine direction 32) of the folding skis 44 and folding boards 46 may be controlled according to the number and location of the folds to be formed in the form-on web 16. Examples of a form-on web 16 that may be output from the pleating unit 30 are illustrated in FIGS. 4-6, according to embodiments. As shown with the illustrated examples, the number and/or location of folds 50 formed in the form-on web 16 may be varied based on the configuration of the pleating unit 30, to provide a continuous pleated form-on web 52 of a desired configuration.

Referring again now to FIG. 2, upon exiting the pleating unit 30, the pleated form-on web 52 may advance to a unit 54 that helps to set or retain the folds 50 in the web in place, according to one embodiment. A unit 54 configured to set or retain the folds in place is shown FIG. 2, with it recognized that such a unit 54 may be included or omitted based on the specific configuration of the apparatus 12, including the configuration of the form-on web 16 (e.g., material properties or thickness of the form-on web 16) and the distance between the pleating unit 30 and the forming drum 24. In embodiments of the apparatus 12 where such a unit 54 is included, the unit 54 may function to set or retain the folds 50 in the pleated form-on web 52 via a number of different mechanisms. In one embodiment, the unit 54 may be provided as a heated roller that the pleated form-on web 52 is passed over as it advances in the machine direction 22. The heated roller may be positioned adjacent the top surface of the pleated form-on web 52 to apply heat to the web, thereby further "setting" the folds 50 in place as the pleated form-on web 52 continues to advance in the machine direction 22. In one example, the heated roller may be configured to intermittently apply heat and pressure at spaced apart intervals on the web 52. In another embodiment, the unit 54 may be provided as a bonding unit that forms weak bonds on the pleated form-on web 52 that bond the overlapped portion(s) of material together. The bonds temporarily retain the folds 50 in place as the pleated form-on web 52 continues to advance in the machine direction 22, until a force of sufficient magnitude acts on the web that cause the tack bonds to break. In yet another embodiment, the unit 54 may be provided as an adhesive applicator configured to dispense a fugitive adhesive according to a predetermined pattern. According to embodiments, the bonds may be formed via application of a fugitive adhesive, tack bonding, a needle punch, or static pin bonding, as non-limiting examples.

According to the illustrated embodiment, the apparatus 12 also includes an adhesive applicator 56 that is positioned downstream from the pleating unit 30 (and downstream from the unit 54, if included in the apparatus 12) that applies adhesive 58 (FIGS. 4-6) to a top surface of the pleated form-on web 52, although it is recognized that such an adhesive applicator 56 is not required. In some examples, the adhesive 58 may be a hot-melt adhesive, such as either a contact hot-melt adhesive or a non-contact hot-melt adhesive. In other examples, adhesive 58 may be any other suitable adhesive for application on a nonwoven web. Further, the adhesive 58 may be applied using any suitable application technique or techniques, including a spray application, a slot-coat application, or another appropriate application technique.

According to embodiments, the adhesive 58 is applied to the pleated form-on web 52 according to a pattern that is determined based on the number and location of folds 50 formed in the pleated form-on web 52, as shown in shown in FIGS. 4-6. Specifically, the adhesive 58 is applied to the pleated form-on web 52 in a pattern that defines adhesive zones 59a and adhesive-free zones 59b, with the adhesive zones 59a aligned with non-overlapped portions of the pleated form-on web 52 and the adhesive-free zones 59b aligned with overlapped portions of the pleated form-on web 52. Examples of patterns in which adhesive 58 is applied to the pleated form-on web 52 are shown in FIGS. 4-6, with it being seen therein that the adhesive 58 is not applied to locations (in the cross-machine direction 32) where folds 50 are formed in the pleated form-on web 52, but only to non-overlapped portions of the pleated form-on web 52.

Referring again to FIG. 2, after adhesive 58 is applied to the pleated form-on web 52, the web 52 continues downstream in the machine direction 22 and is brought into proximity to the forming drum 24, where the pleated form-on web 52 is then drawn onto the forming drum 24 via vacuum pressure. As shown in FIG. 2, and now also in FIG. 7, an example forming drum 24 may include a movable, cylindrical outer forming surface 60 extending around the circumference of the forming drum 24. The forming drum 24 is mounted on a drive shaft 28 that is driven in rotation by a suitable motor (not shown) to rotate the forming drum 24 in direction 26, so as to coincide with and match the translation of the form-on web 16 in the machine direction 22.

A vacuum system 62 is located radially inwardly of the forming surface 60 that is in fluid communication with the forming surface 60 for drawing air through vacuum openings 64 formed therein. The vacuum system 62 includes a suitable arrangement of ducts or conduits (not shown) that extend between the forming surface 60 and a vacuum source 66 (e.g., an exhaust fan), such that a vacuum may be communicated to the forming surface 60. The vacuum communicated to the forming surface 60 acts to suction the form-on web 16 to the forming drum 24 as the form-on web 16 advances around the forming drum 24 and also helps to pull absorbent particulate material to the forming surface 60, as will be explained further below.

According to embodiments, the forming surface 60 is configured to include one or more depressions or pockets 68 defined on the circumferential surface thereof in which absorbent cores are formed. The one or more depressions 68 extend and/or are aligned along the circumferential dimension (i.e., machine direction 22). In the illustrated embodiment, a single, continuous depression 68 is defined on the forming surface 60 in which a continuous absorbent core is formed (that can be later segmented or cut into discrete pads). In other embodiments, it is recognized that a plurality of discrete depressions 68 may be defined in the forming surface 60 and aligned in the circumferential dimension in which discrete absorbent cores are formed.

In order to define the depression 68 in the forming surface 60, an arrangement of cover plates 70 may be attached to the forming drum 24 on the forming surface 60. The cover plates 70 may be operatively held and mounted on the forming surface 60 by employing any suitable attachment mechanism, including a system of nuts and bolts or other fasteners, as non-limiting examples. The cover plates 70 cover a portion of the forming surface 60 in order to block the vacuum in particular portions of the forming surface 60. The cover plates 70 define the depression 68 and provide for communication of the vacuum at the locations of the depression 68, with the cover plates 70 allowing for differently shaped absorbent cores to be formed on the forming drum 24 depending on the specific configuration or construction of the cover plates 70.

Figure 7:
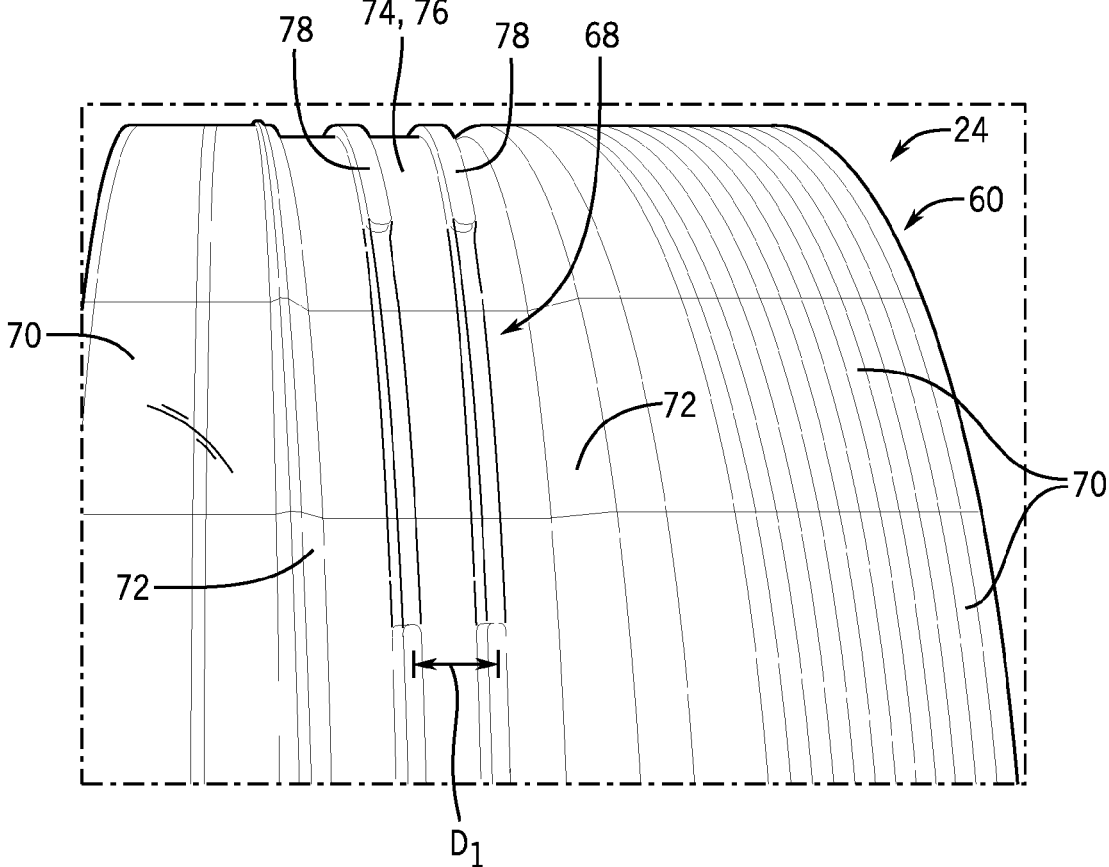
FIG. 7 is a detailed perspective view of a portion of the forming drum included in the apparatus of FIG. 2, illustrating a depression and inserts provided on the forming drum for forming an absorbent core, according to an embodiment of the invention.

As shown in FIG. 7 and also in FIGS. 8-14, a cover plate 70 is configured to define a three-dimensional depression 68 that is defined by one or more side walls 72 and a floor 74. The side walls 72 define the shape of the depression 68 (and of the resulting absorbent core that is produced), and the walls 72 may be formed as vertical walls or as sloped walls, according to embodiments. The height of the walls 72, and corresponding depth of the depression 68, may vary depending upon the particulars of the manufacturing process for forming the absorbent cores, including the dimensions and/or type of form-on web 16 and the desired thickness of the absorbent core to be formed, as examples.

The floor 74 of the depression 68 includes a baffle or screen 76 that permits airflow therethrough, such that a vacuum can be communicated through the forming surface 60 (i.e., vacuum openings 64) and through the floor 74. A vacuum that is communicated through the floor 74 allows for the form-on web 16 to be suctioned down into the depression 68 and retained therein and also allows absorbent particulate material that is deposited into the depression 68 (on the form-on web 16) to be retained.

For those cover plates 70 positioned at locations in the circumferential dimension along the forming drum 24 at which given discrete cores are to be formed (from the continuous core), the cover plate 70 is further configured to include an arrangement of one or more protrusions or inserts 78 in the depression 68 that aid in forming channels in the absorbent core that are free or substantially free of absorbent material (see channels 10 in FIG. 1, for example). In the illustrated embodiment, two inserts 78 are included in the depression 68, but it is recognized that a single insert 78 or more than two inserts 78 could alternately be provided. The inserts 78 extend radially outward from the floor 74 of the depression 68 and, in one embodiment, the height of the inserts 78 is equal to a height of the walls 72. The inserts 78 are arranged so as to be generally oriented in the machine direction 22, with the inserts 78 spaced apart from each other in the cross-machine direction 32 by a distance D1. In the illustrated embodiment, the inserts 78 have a generally linear shape, but it is envisioned that the inserts 78 could alternatively have a non-linear shape. With only a portion of the cover plates 70 including inserts 78, the sets of inserts 78 provided on the forming drum 24 are therefore spaced apart in the circumferential dimension (i.e., the machine direction 22).

Figures 8, 9, 10:
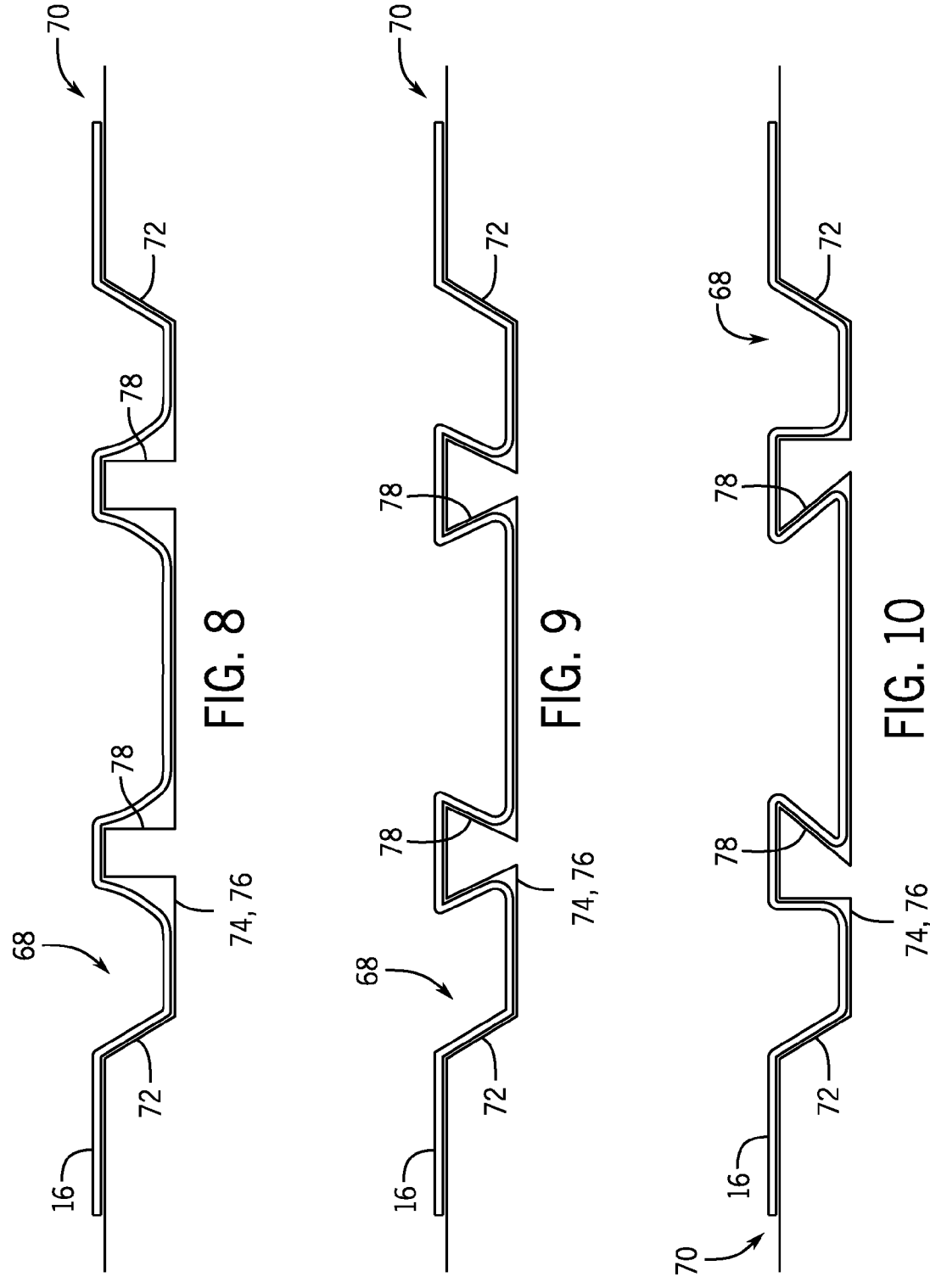
FIG. 8 depicts an end view of inserts included in the forming drum depression, and conforming of a form-on web within the depression, according to an embodiment of the invention.
FIG. 9 depicts an end view of inserts included in the forming drum depression, and conforming of a form-on web within the depression, according to an embodiment of the invention.
FIG. 10 depicts an end view of inserts included in the forming drum depression, and conforming of a form-on web within the depression, according to an embodiment of the invention.

Examples of inserts 78 that may be provided in the depression 68 are illustrated in FIGS. 8-10, according to embodiments of the invention. FIG. 8 illustrates inserts having a rectangular cross-section, along with a resulting conformity of the form-on web 16 to the inserts 78 and the floor 74 of the depression 68. FIG. 9 illustrates inserts having a cross-section that may be described as an inverted isosceles or equilateral triangular shape, along with a resulting conformity of the form-on web 16 to the inserts 78 and the floor 74 of the depression 68. FIG. 10 illustrates inserts having a cross-section that may be described as an inverted right triangle shape (with angles surface of the inserts facing each other), along with a resulting conformity of the form-on web 16 to the inserts 78 and the floor 74 of the depression 68.

It is recognized that the various design and construction of the inserts 78 implemented in the forming drum 24 may be selected based on various design considerations, including ease of manufacturing and the amount of conformity provided about the inserts 78 for the form-on web 16, as examples. The inserts 78 of FIG. 8 may provide ease in manufacturing, while the inserts 78 of FIG. 9 provide greater conformity of the form-on web 16 about the inserts 78 and to the floor 74 and the inserts 78 of FIG. 10 provide for greater conformity of the form-on web 16 about the inserts 78 and to the floor 74 (as compared to the inserts 78 of FIG. 8) while also providing for a maximum free-swell of absorbent particulate material between channels 10 in the resulting absorbent core 2.

Figures 11, 12, 13A, 13B, 14A, 14B:
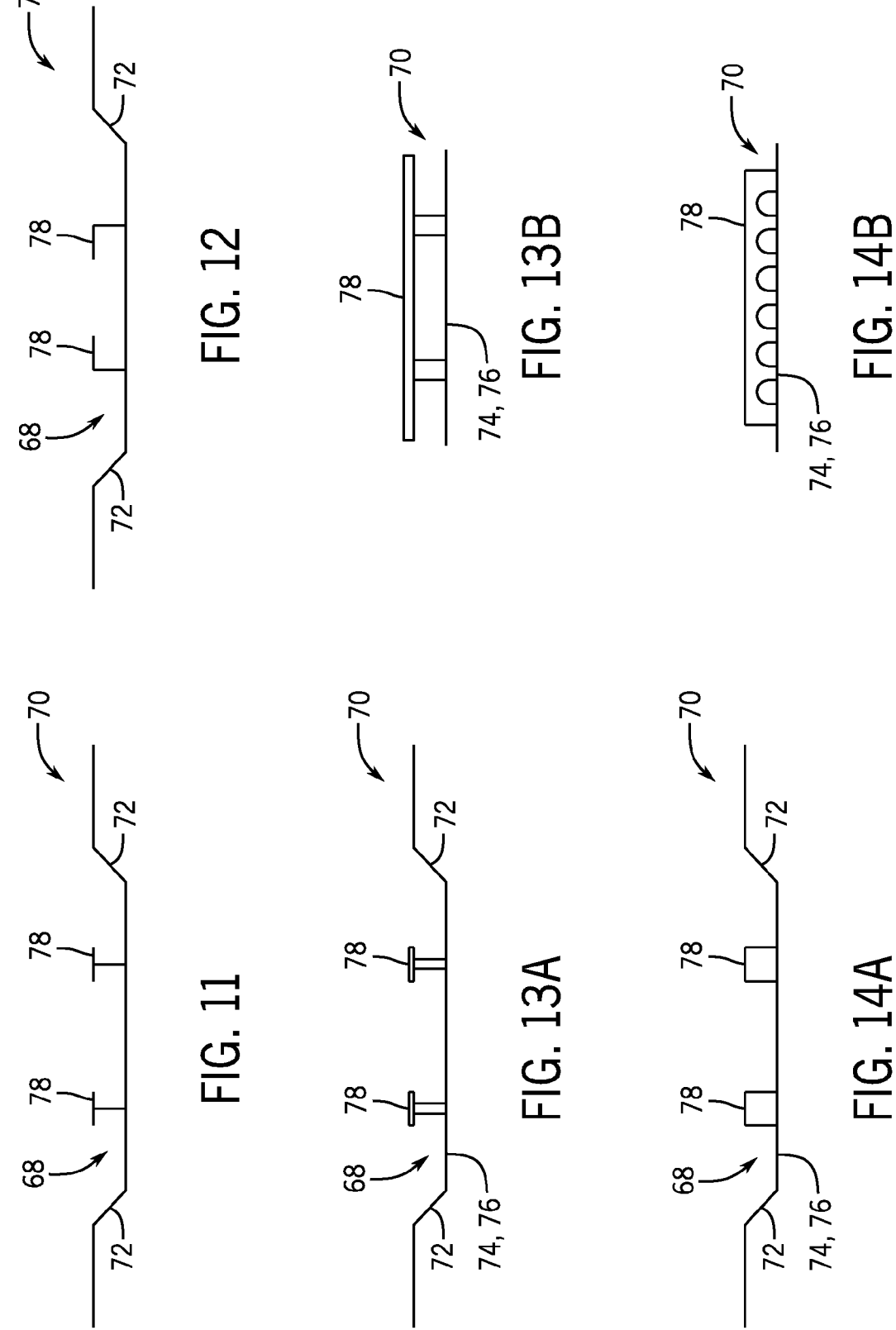
FIG. 11 depicts an end view of inserts included in the forming drum depression, according to an embodiment of the invention.
FIG. 12 depicts an end view of inserts included in the forming drum depression, according to an embodiment of the invention.
FIGS. 13A and 13B depict an end view and side view, respectively, of inserts included in the forming drum depression, according to an embodiment of the invention.
FIGS. 14A and 14B depict an end view and side view, respectively, of inserts included in the forming drum depression, according to an embodiment of the invention.

Still additional examples of inserts 78 that may be provided in the depression 68 are illustrated in FIGS. 11-14, according to embodiments of the invention. FIGS. 11 and 12 illustrate inserts having a T-shaped cross-section and an inverted L-shaped cross-section, respectively, where the inserts 78 provide for greater conformity of the form-on web 16 about the inserts 78 and to the floor 74. FIGS. 13A and 13B illustrate inserts 78 having a pedestal type construction, where an upper surface is raised up off the floor by a pair of supports. FIGS. 14A and 14B illustrate inserts 78 having an upper surface supported by a base structure having ventilation channels formed therein. For each of the inserts 78 in FIGS. 13A and 13B and FIGS. 14A and 14B, an airflow is thus provided through the base of the inserts 78, i.e., an airflow through a space between the supports or through the ventilation channels, with this air flow further enhancing conformity of the form-on web 16 about the inserts 78 and to the floor 74.

Referring now to FIGS. 15-18 a feeding of the pleated form-on web 52 onto the forming drum 24 relative to a depression 68 (and inserts 78 therein) is illustrated, at different points of the feeding process and according to different embodiments. According to the embodiments, the pleated form-on web 52 is fed onto the forming drum 24 such that the folds 50 in the pleated form-on web 52, along with the adhesive 58 deposited thereon, are aligned with the inserts 78 in the depression 68 in a desired manner. The folds 50 in the pleated form-on web 52 unfold as the pleated form-on web 52 is suctioned down into the depression 68, so as to enable the pleated form-on web 52 to better conform to the walls 72 and inserts 78 of the depression 68 and reduce the amount of cross-direction stress and tension present in the web.

Figure 15:
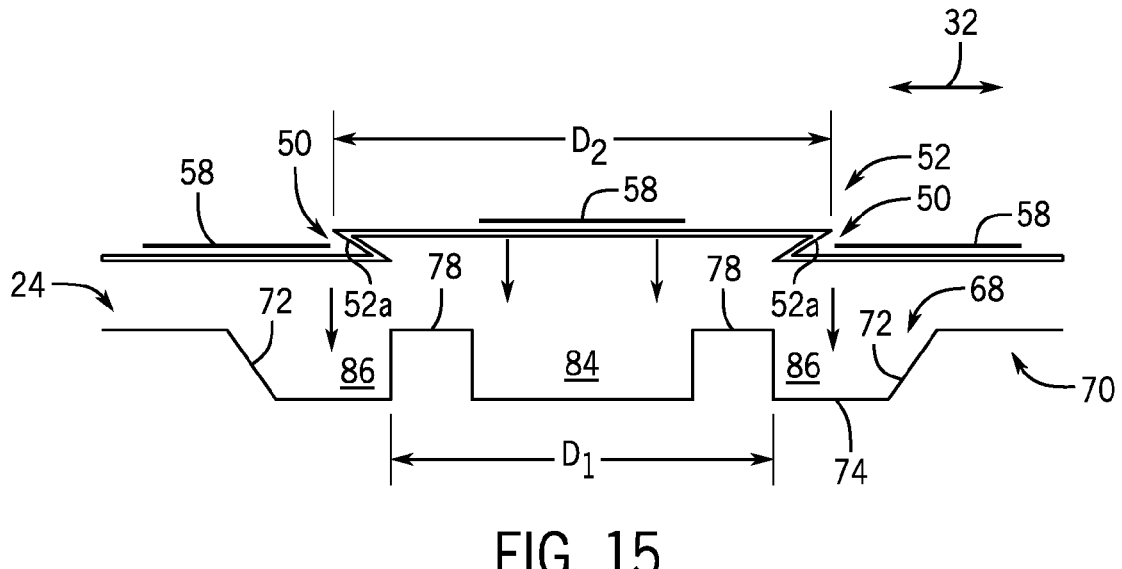
FIG. 15 illustrates a pleated web of nonwoven material aligned with a depression of the forming drum of FIG. 2, according to an embodiment of the invention.
Figure 16:
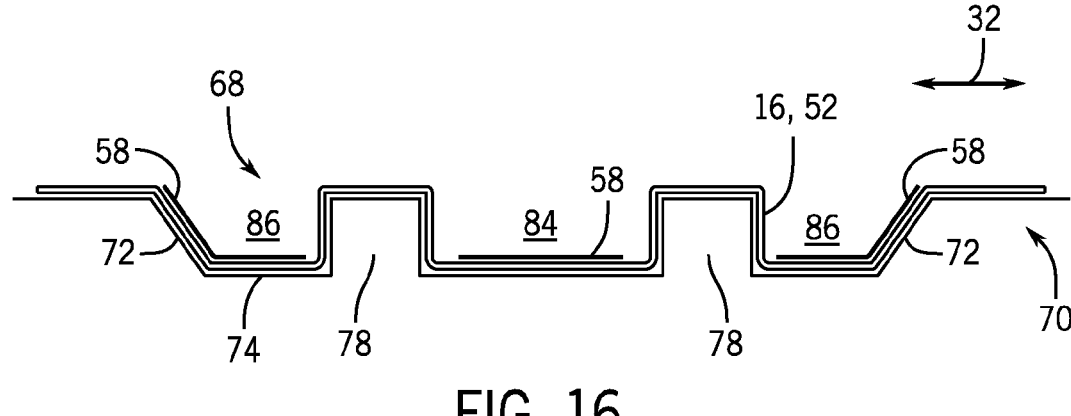
FIG. 16 illustrates the pleated web of FIG. 15 after being fed into the depression and being conformed thereto via suction.

Referring first to FIGS. 15 and 16, a pleated form-on web 52 is shown as being fed onto the forming drum 24 where the pleated form-on web 52 includes a pair of machine direction folds 50 formed therein. As shown in FIG. 15, the pleated form-on web 52 is fed onto the forming drum 24 such that it is generally aligned in the cross-machine direction 32 with the depression 68 defined by cover plates 70 and provided on the forming surface 60. More specifically, the pleated form-on web 52 is fed onto the forming drum 24 such that such that the folds 50 in the pleated form-on web 52 and the adhesive 58 are aligned with the inserts 78 in the depression 68 in a desired manner. Regarding the folds 50, the folds 50 are formed such that the outward-facing edges 52a of the pleat are spaced apart in the cross-machine direction 32 by a distance D2 that is greater than the distance D1 between the outward-facing surfaces of the inserts 78. The pleated form-on web 52 is aligned with the inserts 78 such that the outward-facing surfaces of the inserts 78 are positioned between the outward-facing edges 52a of the pleat in the cross-machine direction 32. Regarding the adhesive 58, the pleated form-on web 52 is aligned with the inserts 78 such that the adhesive 58 applied on the pleated form-on web 52 is offset from the inserts 78 in the cross-machine direction 32.

As the pleated form-on web 52 is drawn onto the forming drum 24 and is suctioned down into the depression 68 (via operation of vacuum system 62, FIG. 2), the pleated form-on web 52 unfolds, as shown in FIG. 16. Specifically, the folds 50 are caused to unfold downwardly (i.e., radially inward toward the floor 74 of the depression) as the pleated form-on web 52 is suctioned down into the depression 68. As the pleated form-on web 52 unfolds, the width of the web thus increases in the cross-machine direction 32 and allows the web to better conform to the walls 72, floor 74, and inserts 78 of the depression 68. In unfolding in this manner, the adhesive 58 on the form-on web 16 gets positioned within the depression 68 at locations offset from the inserts 78 in the cross-machine direction 32, with the adhesive 58 adjacent regions of the walls 72 and the floor 74.

Figure 17:
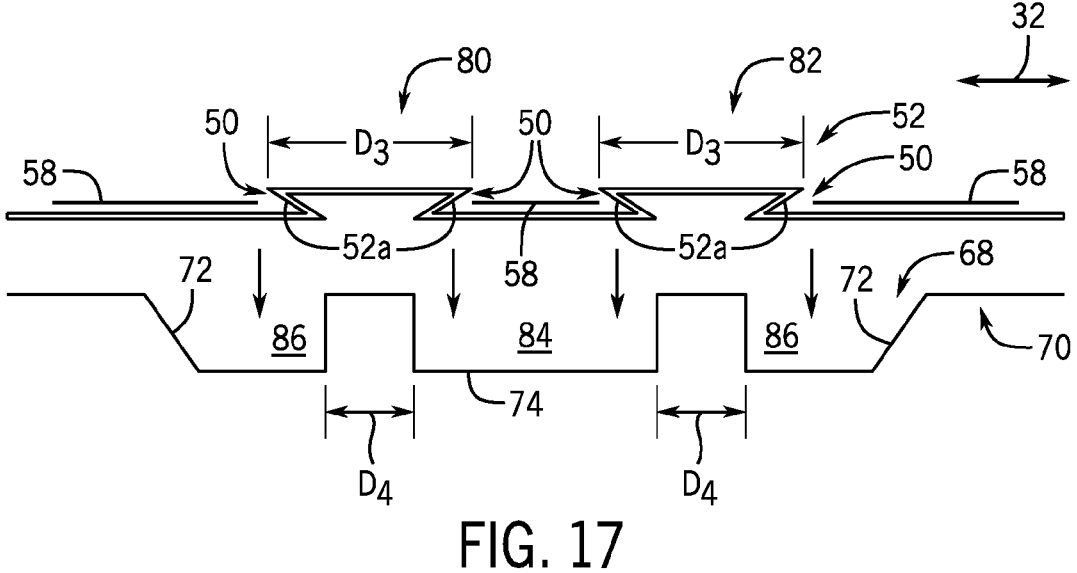
FIG. 17 illustrates a pleated web of nonwoven material fed into a depression of the forming drum of FIG. 2, according to another embodiment of the invention.
Figure 18:
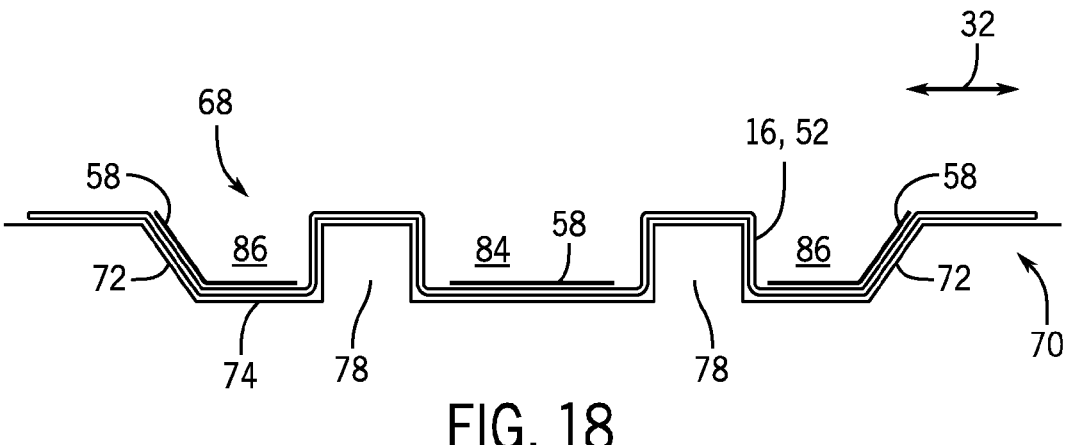
FIG. 18 illustrates the pleated web of FIG. 17 after being fed into the depression and being conformed thereto via suction.

Referring now to FIGS. 17 and 18, a pleated form-on web 52 is shown as being fed onto the forming drum 24 where the pleated form-on web 52 includes four machine direction folds 50 formed therein that define two different pleated areas 80 and 82. As shown in FIG. 17, the pleated form-on web 52 is fed onto the forming drum 24 such that it is generally aligned in the cross-machine direction 32 with the depression 68 defined by cover plates 70 and provided on the forming surface 60. More specifically, the pleated form-on web 52 is fed onto the forming drum 24 such that such that the folds 50 in the pleated form-on web 52 and the adhesive 58 are aligned with the inserts 78 in the depression 68 in a desired manner. Regarding the folds 50, the folds 50 in the first pleated area 80 are formed such that outward-facing edges 52a of the pleat are spaced apart in the cross-machine direction 32 by a distance D3 that is greater than the width of an individual insert 78 D4, while the folds 50 in the second pleated area 82 are similarly formed such that outward-facing edges 52a of the pleat are spaced apart in the cross-machine direction 32 by a distance D3 that is greater than the width of an individual insert 78. The pleated form-on web 52 is aligned with the inserts 78 such that the folds 50 of the first pleated area 80 are positioned about a first one of the inserts 78 in the cross-machine direction 32 and the folds 50 of the second pleated area 82 are positioned about a second one of the inserts 78 in the cross-machine direction 32. Regarding the adhesive 58, the pleated form-on web 52 is aligned with the inserts 78 such that the adhesive 58 applied on the pleated form-on web 52 is offset from the inserts 78 in the cross-machine direction 32.

As the pleated form-on web 52 is drawn onto the forming drum 24 and is suctioned down into the depression 68 (via operation of vacuum system 62, FIG. 2), the pleated form-on web 52 unfolds downwardly as shown in FIG. 18. As the pleated form-on web 52 unfolds, the width of the web thus increases in the cross-machine direction 32 and allows the web to better conform to the walls 72, floor 74, and inserts 78 of the depression 68. In unfolding in this manner, the adhesive 58 on the form-on web 16 gets positioned within the depression 68 at locations offset from the inserts 78 in the cross-machine direction 32, with the adhesive 58 adjacent regions of the walls 72 and the floor 74.

In feeding and suctioning the pleated form-on web 52 onto the forming drum 24 and down into the depression 68 as shown in FIGS. 15-18, the vacuum communicated to the depression 68 may be selectively controlled to better conform the web to the floor 74 and about the inserts 78. According to embodiments, the vacuum communicated to the depression 68 may be controlled in a phased progression that begins by communicating vacuum to a center region 84 of the depression 68 (between inserts 78) and continues by communicating vacuum to side regions 86 of the depression 68 (outside of inserts 78) flanking the center region 84 in the cross-machine direction 32. By selectively controlling the communication of vacuum to the center region 84 and side regions 86 of the depression 68, the stress and tension experienced by the pleated form-on web 52 as it is drawn down into the depression 68 and conforms to the floor 74 and about the inserts 78 can be reduced, thereby reducing the occurrence of tears in the web 52 during fabrication of the absorbent cores 2.

Figures 19, 20, 21:
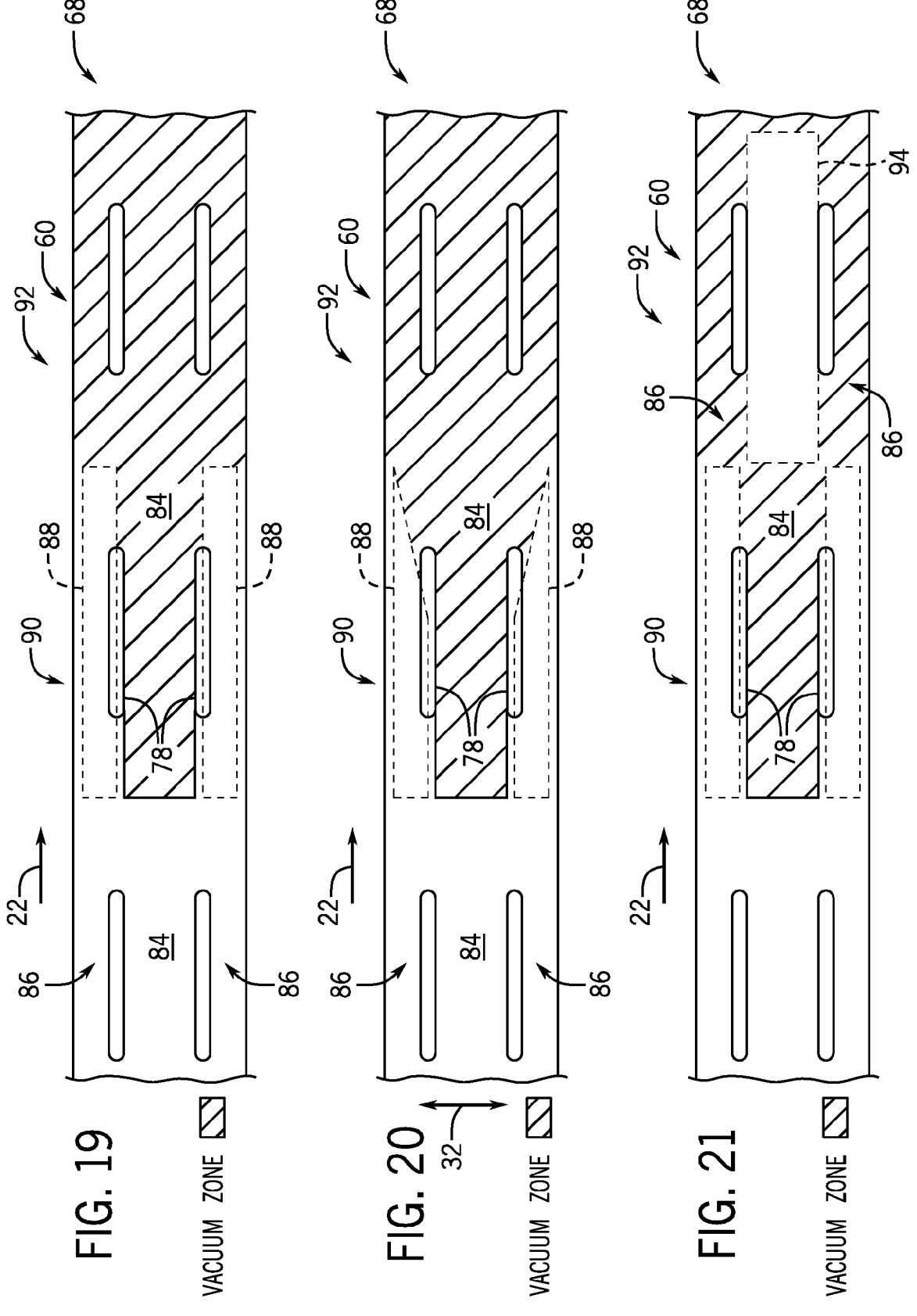
FIG. 19 is a laid-out view of a depression of the forming drum of FIG. 2 and a positioning of a vacuum shoe relative thereto, according to embodiment of the invention.
FIG. 20 is a laid-out view of a depression of the forming drum of FIG. 2 and a positioning of a vacuum shoe relative thereto, according to embodiment of the invention.
FIG. 21 is a laid-out view of a depression of the forming drum of FIG. 2 and a positioning of a pair of vacuum shoes relative thereto, according to embodiment of the invention.

As shown in FIG. 2, and now also in FIGS. 19-21, the vacuum system 62 further includes one or more vacuum shoes 88 (positioned beneath the cylindrical outer forming surface 60 in a stationary manner) that are configured to selectively allow a phased, progressive communication of vacuum to the center region 84 and side regions 86 of the depression 68 as a portion of the depression 68 aligns with the vacuum shoe 88. In one embodiment, a vacuum shoe 88 is provided in the forming drum 24 at a lay-down zone location 90 at which the pleated form-on web 52 is fed onto the forming drum 24, with the vacuum shoe 88 only allowing a vacuum to be communicated to the center region 84 of the depression. By limiting the vacuum suction to only the center region 84, the pleated form-on web 52 is initially drawn down into the center region 84 and may begin to conform to the floor 74 in the center region 84 and about the inserts 78 while experiencing reduced stress and tension in the cross-machine direction 32.

Upon initially drawing down the pleated form-on web 52 into the center region 84, the vacuum communicated to the depression 68 may be modified such that a vacuum may be communicated to both the center region 84 and the side regions 86, or to only the side regions 86, of the depression 68. That is, a pattern of vacuum communicated to the depression 68 may switch from a first vacuum communication pattern at the lay-down zone location 90 to a second vacuum communication pattern at a mixing zone location 92 that is downstream in the machine direction 22 from the lay-down zone location 90, with the form-on web 16 being fully conformed to the mixing zone location 92 just prior to deposition of absorbent particulate material thereon. As explained below, the modification of the pattern of vacuum communicated to the depression 68 may be accomplished by the use of just the vacuum shoe 88, or by use of both the vacuum shoe 88 and a second vacuum shoe 94.

In one embodiment, and as shown in FIG. 19, the vacuum shoe 88 is configured to provide an abrupt change from the first vacuum communication pattern at the lay-down zone location 90 to the second vacuum communication pattern at the mixing zone location 92. That is, the vacuum shoe 88 is structured to provide a constant first vacuum communication pattern, with edges of the vacuum shoe 88 aligned in parallel with the side regions 86 of the depression 68 and covering these side regions 86. As the forming drum 24 (i.e., the forming surface 60 thereof) rotates in the machine direction 22 past an ending of the vacuum shoe 88 and to the mixing zone location 92, the vacuum shoe 88 terminates and the second vacuum communication pattern is allowed where vacuum is then communicated to both the center region 84 and the side regions 86 of the depression 68.

In another embodiment, and as shown in FIG. 20, the vacuum shoe 88 is configured as a tapered vacuum shoe that provides a transition from the first vacuum communication pattern at the lay-down zone location 90 to the second vacuum communication pattern at the mixing zone location 92 that is downstream in the machine direction 22 from the lay-down zone location 90. That is, the vacuum shoe 88 is configured to gradually expand the area in the depression 68 to which vacuum is communicated, with the vacuum shoe 88 tapering outwards in the cross-machine direction 32 such that vacuum communication to the depression 68 may transition from just being provided in the center region 84 to both the center region 84 and the side regions 86. A first vacuum communication pattern provided by the vacuum shoe 88 (at a first end thereof) allows a vacuum to be communicated only to the center region 84 of the depression 68 while blocking vacuum to the side regions 86, as described above. As the vacuum shoe 88 tapers outward, the area in the depression 68 to which vacuum is communicated is gradually expanded, with the vacuum shoe 88 tapering outwards such that vacuum to the side regions 86 is no longer blocked by the vacuum shoe 88. As the forming drum 24 (i.e., the forming surface 60 thereof) rotates in the machine direction 22 past an ending of the vacuum shoe 88 and to the mixing zone location 92, the vacuum shoe 88 terminates and a second vacuum communication pattern is allowed where vacuum is communicated to both the center region 84 and the side regions 86 of the depression 68.

In another embodiment, and as shown in FIG. 21, a second vacuum shoe 94 is provided in the forming drum 24 at the mixing zone location 92 that is distinct from the vacuum shoe 88. The vacuum shoe 88 is structured to provide a constant first vacuum communication pattern, with edges of the vacuum shoe 88 aligned in parallel with the side regions 86 of the depression and covering these side regions 86. As the forming drum 24 (i.e., the forming surface 60 thereof) rotates in the machine direction 22 past an ending of the vacuum shoe 88 and to the mixing zone location 92, the vacuum shoe 88 terminates and the second vacuum shoe 94 is then aligned with a same portion the depression 68. The second vacuum shoe 94 is structured to provide a second vacuum communication pattern where vacuum is communicated to only the side regions 86 of the depression 68, while the second vacuum shoe 94 blocks vacuum from the center region 84.

By selectively phasing the vacuum communicated to the depression 68 via the embodiments shown and described in FIGS. 19-21, a two-stage drawdown of the pleated form-on web 52 into the depression 68 is provided. In a first stage of the drawdown, the pleated form-on web 52 may first be seated into the center region 84 of the depression 68, between the inserts 78, by selectively communicating a vacuum only to the center region 84, such as via the use of a vacuum shoe 88. In being seated in the center region 84, the folds 50 of the pleated form-on web 52 unfold and the web conforms to the floor 74 in the center region 84 and about the inserts 78, with this being achieved with minimal strain being placed on the pleated form-on web 52. In a second stage of the drawdown, the remaining portions of the pleated form-on web 52 (adjacent the side regions 86) may then be drawn down into the depression 68 by communicating a vacuum only to the side regions 86 of the depression 68 (by use of a second vacuum shoe 94) or by communicating a vacuum to both the center region 84 and the side regions 86 (with or without a gradual transition between the two vacuum patterns). In being suctioned down to the side regions 86, tension is maintained on the form-on web 16 and the web is secured to the edges of the depression 68 (i.e., to walls 72), without being sucked into the center region 84. The form-on web 16 thus is made to be positioned in and conform to the depression 68 in a desired manner and provide for a subsequent application of absorbent particulate material onto the form-on web 16 (within the depression 68) to provide for fabrication of absorbent cores 2.

Referring again now to FIG. 2, as the forming drum 24 rotates in the direction 26, and with the unfolded form-on web 16 pulled via vacuum into the depression 68 of the forming drum 24, the form-on web 16 enters a particulate material delivery system 96 that is positioned adjacent to a portion of the forming drum 24. Inside of the particulate material delivery system 96, particulates of absorbent material 98 (e.g., the absorbent material 8 of FIG. 1, for example) are deposited onto the form-on web 16. More specifically, the absorbent particulate material 98 is deposited onto the form-on web 16 and within the depression 68 formed on the forming drum 24. Within the depression 68, the absorbent particulate material 98 is delivered onto the adhesive 58 applied on the form-on web 16 so that the particulate material 98 becomes stabilized or immobilized on the form-on web 16 by the adhesive 58.

According to the illustrated embodiment, the particulate material delivery system 96 may perform a single application of absorbent particulate material 98 onto the form-on web 16 within the depression 68. In such an embodiment, a mixture of SAP granules, fluff, and absorbent material binder may be delivered to the delivery system 96 from one or more hoppers 100, with a connecting pipe 102 extending between each hopper 100 and the delivery system 96 in order to transport the particulate material 98 therebetween. In the illustrated embodiment, a single hopper 100 is provided from which the absorbent particulate material 98 is provided to the particulate material delivery system 96. In some embodiments, the connecting pipe(s) 102 may include a metering device (not shown) that operates to ensure that only a specified amount (for instance, by volume or by weight) of particulate material 98 flows through the connecting pipe 102 per unit of time.

According to one embodiment, after absorbent particulate material 98 has been deposited onto the form-on web 16 and within the depression 68 at a desired location, excess particulate material 98 may be removed and/or the top surface of the particulate material smoothed via a scarfing unit 104. The scarfing unit 104 functions to scrape off particulate material 98 that may extend up past the level of the depression 68 (i.e., up past walls 72) and that may be positioned atop inserts 78, with the removed particulate material 98 being discharged and recycled back into the system through a discharge 106.

After exiting the particulate material delivery system 96, the form-on web 16, now containing adhesive 58 and particulate material 98, proceeds to a location 108 on the forming drum 24 where a second continuous web of non-woven material 110 (hereafter, a "cover web 110" for purposes of simplicity) is applied thereto. The cover web 110 may be unwound from a roll 112 of cover web material and may be transported proximate the forming drum 24 via one or more material handling rollers 114.

As the cover web 110 is being advanced by the material handling roller(s) 114 toward the forming drum 24, an adhesive applicator 116 applies adhesive to the cover web 110. In some examples, the adhesive may be a hot-melt adhesive, such as either a contact hot-melt adhesive or a non-contact hot-melt adhesive, with the adhesive being applied using any suitable application technique or techniques, including a spray application, a slot-coat application, or another appropriate application technique. In some embodiments, the adhesive is applied to the cover web 110 according to a "dual pattern" type application. That is, the adhesive applicator 116 may be configured to apply adhesive to the cover web 110 in a continuous, all-over pattern on some sections of the web and apply adhesive to the cover web 110 in an intermittent pattern on some other sections of the web. The intermittent adhesive pattern may correspond to locations on the forming drum 24 where inserts 78 are present in the depression 68, with no adhesive being applied on the cover web 110 at locations that coincide with the inserts 78, such that channels 10 formed in the absorbent cores 2 (FIG. 1) will be free of adhesive. In yet other examples, adhesive applicator 116 may be omitted entirely.

After the cover web 110 has reached the location 108 and been applied onto the form-on web 16 and particulate material 98, the cover web 110 is bonded to the form-on web 16 and the absorbent particulate material 98. To facilitate this bonding, a nip roll 118 may be positioned immediately downstream from the location 108 that acts to press the cover web 110 down onto the form-on web 16 and particulate material 98. The nip roll 118 thus causes the adhesive applied onto the cover web 110 to adhere to the form-on web 16 and particulate material 98, thereby forming a continuous absorbent core (or discrete absorbent cores, such as the absorbent core 2 illustrated in FIG. 1).

Upon adhering the cover web 110 to the form-on web 16 and particulate material 98, the resulting absorbent core(s) 2 may be transferred off of the forming drum 24 and onto an adjacent transfer drum 120. In one embodiment, the transfer drum 120 may include a knife or other cutting element 122 thereon (or adjacent thereto) that cuts a continuous absorbent core (formed in the continuous depression 68) into discrete pads, such as absorbent cores 2. The discrete absorbent cores 2 are rotated along the face of the transfer drum 120 and subsequently deposited onto a conveyer 124, for example, for further processing.

The apparatus 12 described above is therefore operable to perform a method of forming and providing a pleated web of material 52 to a core-forming drum 24, as part of the manufacture of an absorbent core 2. The apparatus 12 operates to convey a continuous web of material 16 in a machine direction 22 and operate a pleating unit 30 to form one or more folds 50 in the continuous web of material 16 running in the machine direction 22, the one or more folds 50 providing a continuous pleated web of material 52 with a portion of the continuous pleated web of material 52 overlapped in a cross-machine direction 32. The apparatus 12 further operates to feed the continuous pleated web of material 52 into at least one depression 68 formed in a circumferential surface 60 of a core-forming drum 24 rotating in the machine direction 22, the at least one depression 68 including one or more inserts 78 protruding radially outward from a floor 74 of the depression 68. In feeding the continuous pleated web of material 52 into the at least one depression 68, regions of the continuous pleated web of material 52 separate as the continuous pleated web of material 52 is drawn down into the at least one depression 68.

While the apparatus 12 described above is indicated as having material rolls 18, 112 that provide a form-on web 16 and separate cover web 110 for fabricating absorbent cores 2, it is recognized that the absorbent cores 2 could be formed using only a single web of material. That is, a single, wider continuous web of material could be provided for the form-on web and folded around the absorbent core downstream of the forming drum to enclose particulate material 98 therein and form the absorbent cores 2.

Figure 22:
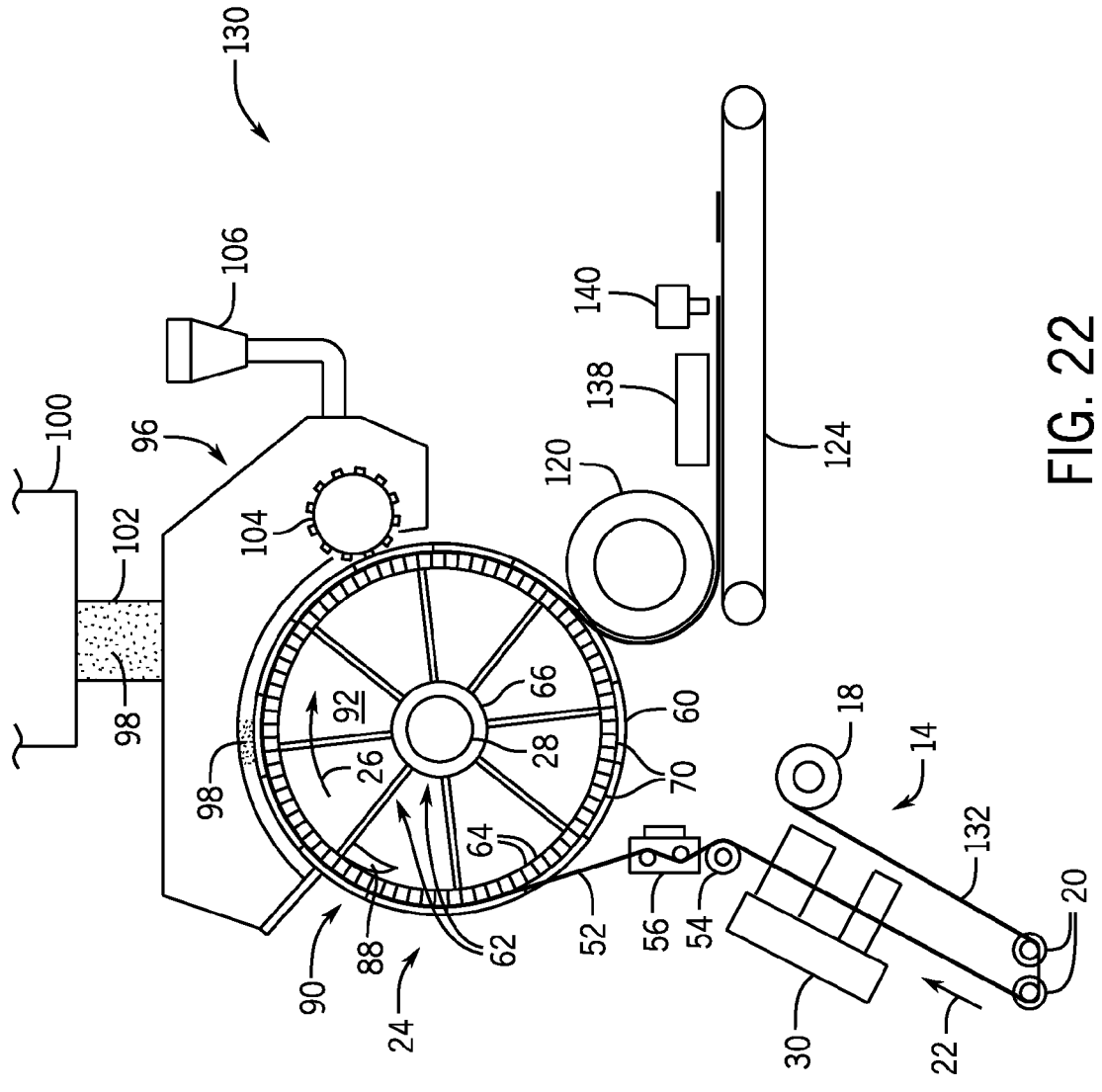
FIG. 22 is a schematic view illustrating the layout of an apparatus for forming a pleated core wrap and applying the pleated core wrap onto a forming drum, according to an embodiment of the invention.

Referring now to FIG. 22, a schematic diagram of an example apparatus 130 is illustrated that may form absorbent cores 2 using only a single material web. The apparatus 130 shares many common components with the apparatus 12 of FIG. 2, and thus like components in apparatus 130 are numbered identically to those in apparatus 12. To facilitate fabrication of absorbent cores 2 using only a single material web, a wide form-on web 132 is provided from a material roll 18. The form-on web 132 can be characterized as including a central section 134 and side sections 136 (FIG. 23) that are arranged side-by-side in the cross-machine direction 32, with the side sections 136 having a width sufficient to provide for a folding-over thereof to cover the central section 134 when folded inwardly.

In operation of the apparatus 130, the form-on web 132 provided by material roll 18 is advanced to the pleating unit 30, with the central section 134 of the web being passed through the pleating unit 30 to form folds 50 therein, as previously described in detail in FIGS. 3A-3C. With the central section 134 thus configured as a pleated web, the form-on web 132 continues downstream, optionally through the adhesive application 56 (where adhesive 58 is applied to the web 132) and to the forming drum 24. The form-on web 132 is drawn onto the forming drum 24 via vacuum, as previously described, with the central section 134 of the form-on web 132 being suctioned down into the depression 68, while the side sections 136 remain outside of the depression 68. Absorbent particulate material 98 is deposited within the depression 68 and onto the central section 134 as the form-on web 132 rotates about the forming drum 24 in the machine direction 22.

Figures 23, 24:
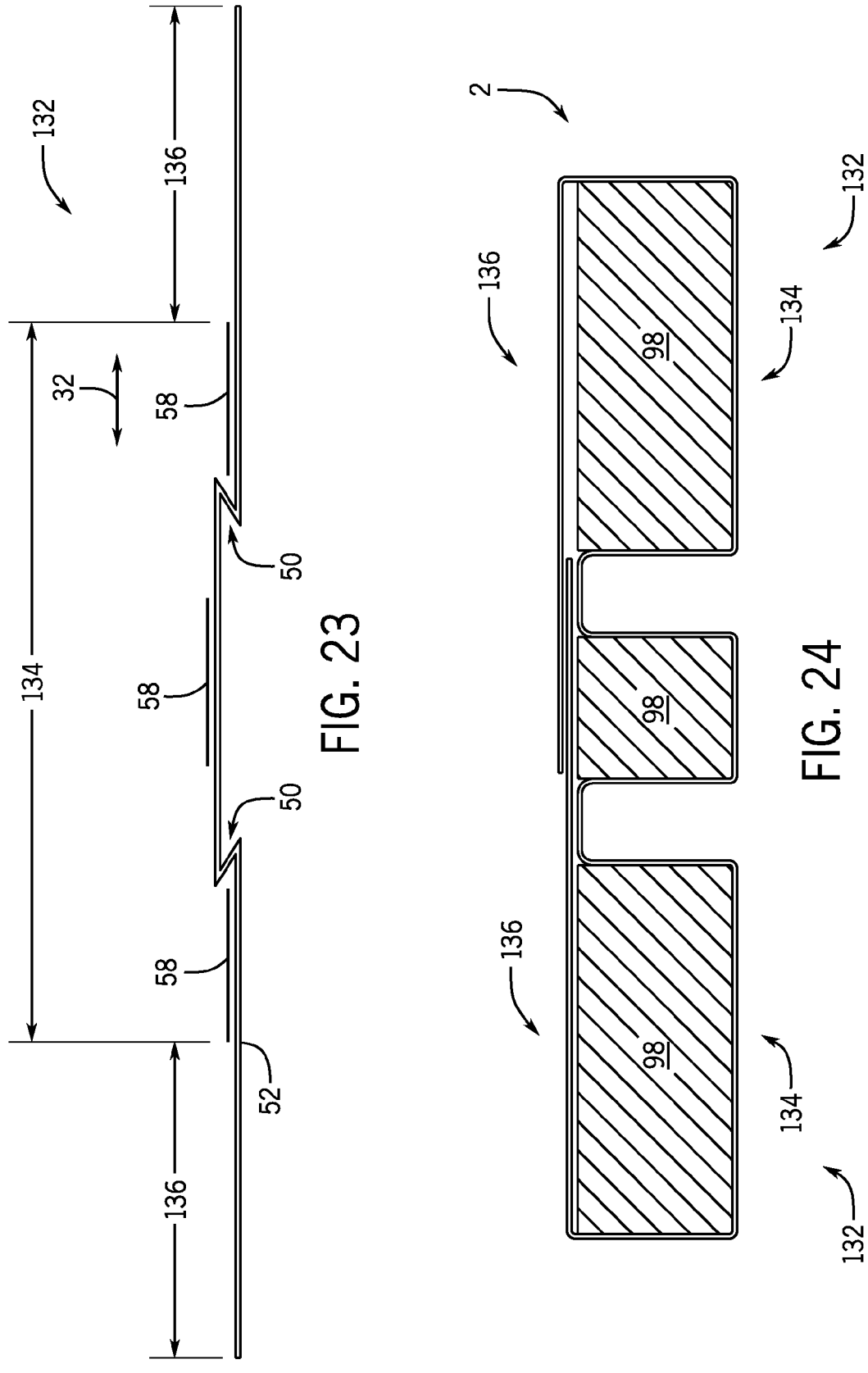
FIG. 23 is a cross-sectional view of a pleated web of nonwoven material that may be provided by any of the pleating units of FIGS. 3A-3C, according to an embodiment of the invention.
FIG. 24 is a cross-sectional view of a channeled absorbent core with a single form-on web wrapped about absorbent particulate material, according to an embodiment of the invention.

Upon rotating to a location adjacent the transfer drum 120, the form-on web 132 and the particulate material 98 contained thereon are transferred off of the forming drum 24 and onto the transfer drum 120. The form-on web 132 and the particulate material 98 are rotated along the face of the transfer drum 120 and subsequently deposited onto a conveyor 124. Upon being deposited onto the conveyor 124, a folding unit 138 acts on the form-on web 132 to fold the side sections 136 over the particulate material 98, such that the particulate material 98 is surrounded by the form-on web 132. According to embodiments, the folding unit 138 may include any known folding device(s), such as one or more plow folding devices, one or more folding boards, or one or more roller edge folding devices, as non-limiting examples. The folding unit 138 folds the side sections 136 inwardly, in the cross-machine direction 32, over and on top of the particulate material 98. The side sections 136 may be of such a width that they overlap each other in the cross-machine direction 32 upon being folded over, as illustrated in FIG. 24 for example.

Upon folding of the form-on web 132, the resulting absorbent core(s) 2 may be cut by a knife or other cutting element 140 thereon that cuts a continuous absorbent core (formed in the continuous depression 68) into discrete pads, such as absorbent cores 2. The discrete absorbent cores 2 may then continue to advance along conveyer 124 for further processing.

Beneficially, embodiments of the invention thus provide an apparatus for forming and applying a pleated core wrap during the manufacture of an absorbent pad. The formation of the pleated core wrap, and subsequent application thereof onto a forming drum, allows the pleated core wrap to better conform to one or more depressions in the forming drum and the inserts included in the depression(s). The pleats in the core wrap reduce the stress and tension placed on the core wrap as the web is laid down into the depression(s), thereby reducing the occurrence of tears in the core wrap during manufacturing of the absorbent pads.

Therefore, according to one embodiment of the invention, an apparatus includes a feeding mechanism configured to feed a continuous web of material in a machine direction and a pleating unit configured to form one or more folds in the continuous web of material, each of the one or more folds comprising a continuous fold running in the machine direction so as to form a continuous pleated web of material with a portion of the web of material overlapped in a cross-machine direction. The apparatus also includes a core-forming drum rotating in the machine direction and positioned downstream in the machine direction from the pleating unit to receive the continuous pleated web of material, the core-forming drum comprising at least one depression provided on an outer circumferential surface of the core forming drum, with the at least one depression including a floor having one or more inserts protruding radially outward therefrom. The apparatus further includes a vacuum system configured to provide a vacuum to the at least one depression, the vacuum communicated through the floor to suction the continuous pleated web of material down into the at least one depression, with regions of the continuous pleated web of material separating upon being suctioned down into the at least one depression.

According to another embodiment of the invention, an apparatus includes a feeding mechanism configured to feed a continuous web of material in a machine direction and a core-forming drum rotating in the machine direction and positioned downstream in the machine direction from the feeding mechanism to receive the continuous web of material, the core-forming drum comprising at least one depression provided on an outer circumferential surface of the core-forming drum, with the at least one depression including a floor having one or more inserts protruding radially outward therefrom. The apparatus also includes a vacuum system that provides a vacuum to the at least one depression, the vacuum communicated through the floor to suction the continuous web of material down into the at least one depression, and wherein the vacuum system is configured to selectively control communication of the vacuum to a plurality of cross-machine direction arranged regions of the at least one depression to provide a multi-stage, progressive laydown of the continuous web of material into the at least one depression.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description but is only limited by the scope of the appended claims.

What is claimed is:

1. An apparatus comprising:
   a feeding mechanism configured to feed a continuous web of material in a machine direction;
   a pleating unit configured to form one or more folds in the continuous web of material, each of the one or more folds comprising a continuous fold running in the machine direction so as to form a continuous pleated web of material with a portion of the web of material overlapped in a cross-machine direction;
   a core-forming drum rotating in the machine direction and positioned downstream in the machine direction from the pleating unit to receive the continuous pleated web of material, the core-forming drum comprising at least one depression provided on an outer circumferential surface of the core forming drum, with the at least one depression including a floor having one or more inserts protruding radially outward therefrom; and
   a vacuum system configured to provide a vacuum to the at least one depression, the vacuum communicated through the floor to suction the continuous pleated web of material down into the at least one depression, with regions of the continuous pleated web of material separating upon being suctioned down into the at least one depression.

2. An apparatus according to claim 1, further comprising an adhesive applicator positioned downstream in the machine direction from the pleating unit, the adhesive applicator configured to apply adhesive to non-overlapped portions of a top surface of the pleated web of material.

3. An apparatus according to claim 2, wherein the adhesive applicator is configured to apply adhesive to non-overlapped portions of the top surface of the pleated web of material that are offset from the one or more inserts in the cross-machine direction.

4. An apparatus according to claim 2, further comprising a heated roller positioned between the pleating unit and the adhesive applicator, the heated roller configured to apply heat to the continuous pleated web of material to set the one or more folds thereof.

5. An apparatus according to claim 2, further comprising a bonding unit positioned between the pleating unit and the adhesive applicator, the bonding unit configured to tack bond the continuous pleated web of material to set the one or more folds thereof.

6. An apparatus according to claim 1, wherein the pleating unit comprises:
   a top roll and a bottom roll positioned to form a nip therebetween through which the continuous web of material is fed, the top and bottom rolls including features thereon that act on the continuous web of material to predispose the continuous web of material to folding; and
   a folding board and one or more folding skis positioned downstream in the machine direction from the top and bottom rolls, the folding board and the one or more folding skis positioned in an overlapped arrangement;
   wherein the continuous web of material is controlled and constrained into a pleated shape when traveling in the machine direction as it passes the one or more folding skis and the folding board.

7. An apparatus according to claim 1, wherein the one or more inserts comprise a first insert and a second insert each generally aligned in the machine direction, with the first insert and the second insert spaced apart in the cross-machine direction by a first distance.

8. An apparatus according to claim 7, wherein the pleating unit is configured to:

form a first fold in the continuous web of material running in the machine direction; and form a second fold in the continuous web of material running in the machine direction;

wherein the first fold and the second fold are spaced apart in the cross-machine direction by a second distance greater than the first distance.

9. An apparatus according to claim 7, wherein the pleating unit is configured to:

form a first pair of folds in the continuous web of material in a first pleated area, each fold of the first pair of folds running in the machine direction; and form a second pair of folds in the continuous web of material in a second pleated area, each fold of the second pair of folds running in the machine direction;

wherein the folds of the first pair of folds are located so as to be positioned on opposing sides of the first insert when the continuous pleated web of material is fed into the at least one depression; and wherein the folds of the second pair of folds are located so as to be positioned on opposing sides of the second insert when the continuous pleated web of material is fed into the at least one depression.

10. An apparatus according to claim 7, wherein the at least one depression comprises a center region positioned between the pair of inserts in the cross-machine direction, and side regions positioned on opposing sides of the center region and outside of the pair of inserts in the cross-machine direction; and wherein the vacuum system is configured to selectively communicate a vacuum to the center region and the side regions.

11. An apparatus according to claim 10, wherein the vacuum system comprises:

a first vacuum shoe positioned at a lay-down zone location of the core-forming drum where the continuous pleated web of material is fed onto the core-forming drum, the first vacuum shoe configured to communicate a vacuum to the center region and block a vacuum to the side regions; and a second vacuum shoe positioned downstream in the machine direction from the first vacuum shoe, the second vacuum shoe configured to communicate a vacuum to the side regions and block a vacuum to the center region.

12. An apparatus according to claim 7, wherein each of the first insert and the second insert has an inverted triangular shape.

13. An apparatus according to claim 7, wherein each of the first insert and the second insert has one or more spaces or ventilation channels formed therein that provides for airflow therethrough.

14. An apparatus comprising:

a feeding mechanism configured to feed a continuous web of material in a machine direction;

a core-forming drum rotating in the machine direction and positioned downstream in the machine direction from the feeding mechanism to receive the continuous web of material, the core-forming drum comprising at least one depression provided on an outer circumferential surface of the core-forming drum, with the at least one depression including a floor having one or more inserts protruding radially outward therefrom; and a vacuum system that provides a vacuum to the at least one depression, the vacuum communicated through the floor to suction the continuous web of material down into the at least one depression;

wherein the vacuum system is configured to selectively control communication of the vacuum to a plurality of cross-machine direction arranged regions of the at least one depression to provide a multi-stage, progressive laydown of the continuous web of material into the at least one depression.

15. An apparatus according to claim 14, wherein the one or more inserts comprise a first insert and a second insert each aligned in the machine direction, with the first insert and the second insert spaced apart in the cross-machine direction by a first distance; and wherein in selectively controlling communication of the vacuum to a plurality of cross-machine direction arranged regions of the at least one depression, the vacuum system is configured to:

initially communicate a vacuum to a center region positioned between the pair of inserts; and subsequently communicate a vacuum to side regions positioned on opposing side of the center region and outside of the pair of inserts in the cross-machine direction, or to both the side regions and the center region.

16. An apparatus according to claim 15, wherein the vacuum system comprises one or more vacuum shoes configured to communicate or block a vacuum to the center region and the side regions.

17. An apparatus according to claim 14, further comprising a pleating unit positioned upstream in the machine direction from the core-forming drum, the pleating unit configured to form one or more folds in the continuous web of material, each of the one or more folds comprising a continuous fold running in the machine direction so as to form a continuous pleated web of material with a portion of the web of material overlapped in a cross-machine direction;

wherein regions of the continuous pleated web of material separate during the multi-stage, progressive laydown of the continuous web of material into the at least one depression.

18. An apparatus according to claim 17, wherein the pleating unit comprises:

a top roll and a bottom roll positioned to form a nip therebetween through which the continuous web of material is fed, the top and bottom rolls including features thereon that act on the continuous web of material to predispose the continuous web of material to folding; and a folding board and one or more folding skis positioned downstream in the machine direction from the top and bottom rolls, the folding board and the one or more folding skis positioned in an overlapped arrangement;

wherein the continuous web of material is controlled and constrained into a pleated shape when traveling in the machine direction as it passes the one or more folding skis and the folding board.

19. An apparatus according to claim 17, further comprising an adhesive applicator positioned downstream in the machine direction from the pleating unit, the adhesive applicator configured to apply adhesive to non-overlapped portions of a top surface of the pleated web of material.

20. An apparatus according to claim 19, wherein the adhesive applicator is configured to apply adhesive to non-overlapped portions of the top surface of the pleated web of material that are offset from the one or more inserts in the cross-machine direction.

* * * * *